US006586661B1

(12) United States Patent
Conkling et al.

(10) Patent No.: US 6,586,661 B1
(45) Date of Patent: Jul. 1, 2003

(54) REGULATION OF QUINOLATE PHOSPHORIBOSYL TRANSFERASE EXPRESSION BY TRANSFORMATION WITH A TOBACCO QUINOLATE PHOSPHORIBOSYL TRANSFERASE NUCLEIC ACID

(75) Inventors: Mark A. Conkling, Fuquay Varina, NC (US); Wen Song, San Diego, CA (US); Nandini Mendu, Durham, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/021,286

(22) Filed: Feb. 10, 1998

Related U.S. Application Data

(60) Provisional application No. 60/049,471, filed on Jun. 12, 1997.

(51) Int. Cl.$^7$ ........................... A01H 5/00; A01H 5/10; C12N 5/14; C12N 15/29; C12N 15/52; C12N 15/82

(52) U.S. Cl. .................... 800/317.3; 800/278; 800/298; 435/320.1; 435/419; 435/468; 435/469; 435/470; 536/23.2; 536/23.6; 47/58.1

(58) Field of Search ................................ 800/278, 285, 800/286, 287, 290, 293, 295, 298, 317.3, 294; 435/69.1, 70.1, 468, 469, 410, 414, 419, 320.1, 470, 375; 536/23.1, 23.2, 23.6

(56) References Cited

U.S. PATENT DOCUMENTS 4,693,976 A 9/1987 Schilperoort
4,762,785 A 8/1988 Comai
4,885,248 A 12/1989 Ahlquist
4,940,838 A 7/1990 Schilperoort et al.
4,945,050 A 7/1990 Sanford et al.
4,954,442 A 9/1990 Gelvin et al.
5,034,322 A 7/1991 Rogers et al.
5,036,006 A 7/1991 Sanford et al.
5,100,792 A 3/1992 Sanford et al.
5,107,065 A 4/1992 Shewmaker et al. ........ 800/205
5,149,645 A 9/1992 Hoekema et al.
5,190,931 A 3/1993 Inouye et al.
5,208,149 A 5/1993 Inouye et al.
5,231,020 A 7/1993 Jorgensen et al.
5,254,800 A 10/1993 Bird et al. .................. 800/205
5,260,205 A 11/1993 Nakatani et al. ............ 435/193
5,272,065 A 12/1993 Inouye et al.
5,283,184 A 2/1994 Jorgensen et al.
5,352,605 A 10/1994 Fraley et al.
5,356,799 A 10/1994 Fabijanski et al. ....... 435/172.3
5,365,015 A 11/1994 Grierson et al. ............ 800/205
5,369,023 A 11/1994 Nakatani et al. ............ 435/193
5,451,514 A 9/1995 Boudet et al. ........... 435/172.3
5,453,566 A 9/1995 Shewmaker et al. ........ 800/205
5,459,252 A 10/1995 Conkling et al.
5,464,763 A 11/1995 Schilperoort et al.
5,501,967 A 3/1996 Offringa et al.
5,530,196 A 6/1996 Fraley et al.
5,610,288 A 3/1997 Rubenstein ................ 536/24.5
5,635,381 A 6/1997 Hooykaas et al.
5,668,295 A 9/1997 Wahab et al.
5,684,241 A 11/1997 Nakatani et al. ............ 800/205
5,693,512 A 12/1997 Finer et al.
5,713,376 A 2/1998 Berger
5,723,751 A 3/1998 Chua
5,731,179 A 3/1998 Komari et al.
5,759,829 A 6/1998 Shewmaker et al.
5,767,378 A 6/1998 Bojsen et al.
5,776,502 A 7/1998 Foulkes et al.
5,776,771 A 7/1998 Yu et al.
5,830,728 A 11/1998 Christou et al.
5,834,236 A 11/1998 Lamb et al.
5,837,876 A 11/1998 Conkling et al.
5,851,804 A 12/1998 Snyder et al.
5,858,742 A 1/1999 Fraley et al.
5,858,774 A 1/1999 Malbon et al.
5,877,023 A 3/1999 Sautter et al.
5,929,306 A 7/1999 Torisky et al.
5,932,782 A 8/1999 Bidney
5,962,768 A 10/1999 Cornelissen et al.
5,976,880 A 11/1999 Sautter et al.
5,981,839 A 11/1999 Knauf et al.
5,989,915 A 11/1999 Christou et al.
5,994,629 A 11/1999 Bojsen et al.
6,022,863 A 2/2000 Peyman
6,051,409 A 4/2000 Hansen et al.
6,051,757 A 4/2000 Barton et al.
6,165,715 A 12/2000 Collins et al.
6,174,724 B1 1/2001 Rogers et al.
6,255,560 B1 7/2001 Fraley et al.
6,271,031 B1 8/2001 Falco et al.
6,281,410 B1 8/2001 Knauf et al.
2001/0006797 A1 7/2001 Kumagai et al.
2001/0026941 A1 10/2001 Held et al.

FOREIGN PATENT DOCUMENTS

CA 1341091 9/2000
EP 0 116 718 A1 8/1984
EP 0 120 515 B1 10/1984
EP 0 120 515 A2 10/1984

(List continued on next page.)

OTHER PUBLICATIONS

Conkling et al. Plant Physiol. 1990. vol. 93, 1203–1211.*
Hughes et al. J. Bacteriology. 1993. Jan. 175:479–486.*
Beck et al, "Nucleotide Sequence and Exact Localization of the Neomycin Phosphotransferase Gene from Transposon Tn 5", Gene, 19: 327–336 (1982).

(List continued on next page.)

*Primary Examiner*—Amy J. Nelson
*Assistant Examiner*—Russell Kallis
(74) *Attorney, Agent, or Firm*—Myers Bigel Sibley & Sajovec, PA

(57) ABSTRACT

DNA encoding a tobacco quinolate phosphoribosyl transferase (QPRTase) enzyme, and constructs comprising such DNA are provided. Methods of altering quinolate phosphoribosyl transferase expression are provided.

32 Claims, 7 Drawing Sheets

FOREIGN PATENT DOCUMENTS

| | | | |
|---|---|---|---|
| EP | 0 120 516 A2 | | 10/1984 |
| EP | 0 131 620 B1 | | 1/1985 |
| EP | 0 131 623 B2 | | 1/1985 |
| EP | 0 131 624 B1 | | 1/1985 |
| EP | 0 140 308 A3 | | 5/1985 |
| EP | 0 140 308 B1 | | 5/1985 |
| EP | 0 140 308 A2 | | 5/1985 |
| EP | 0 159 779 B1 | | 10/1985 |
| EP | 0 176 112 A1 | | 4/1986 |
| EP | 0 189 707 B1 | | 8/1986 |
| EP | 0 223 399 A1 | | 5/1987 |
| EP | 0 224 287 A1 | | 6/1987 |
| EP | 0 240 208 A2 | | 10/1987 |
| EP | 0 240 208 A3 | | 10/1987 |
| EP | 0 240 208 B1 | | 10/1987 |
| EP | 0 265 556 A1 | | 5/1988 |
| EP | 0 270 822 A1 | | 6/1988 |
| EP | 0 290 799 A2 | | 11/1988 |
| EP | 0 290 799 A3 | | 11/1988 |
| EP | 0 320 500 A3 | | 6/1989 |
| EP | 0 320 500 A2 | | 6/1989 |
| EP | 0 131 623 B1 | | 3/1991 |
| EP | 0 458 367 B1 | | 11/1991 |
| EP | 0 458 367 A1 | | 11/1991 |
| EP | 0 467 349 B1 | | 1/1992 |
| EP | 0 486 214 A3 | | 5/1992 |
| EP | 0 486 214 A2 | | 5/1992 |
| EP | 0 486 234 B1 | | 5/1992 |
| WO | WO 84/ 02913 | | 8/1984 |
| WO | WO 84/ 02919 | | 8/1984 |
| WO | WO 84/ 02920 | | 8/1984 |
| WO | WO 90/12084 | | 10/1990 |
| WO | WO 91/02070 | | 2/1991 |
| WO | WO 92/15680 | | 9/1992 |
| WO | WO 93/05163 | | 3/1993 |
| WO | WO 93 0546 A | | 4/1993 |
| WO | WO 93/05646 | * | 4/1993 |
| WO | WO 93/17116 | | 9/1993 |
| WO | WO 94/20627 | | 9/1994 |
| WO | WO 94/26913 | | 11/1994 |
| WO | WO 94 28142 | | 12/1994 |
| WO | WO 94/28142 | | 12/1994 |
| WO | WO 95/16031 | | 6/1995 |
| WO | WO 95/34668 | | 12/1995 |
| WO | WO 95/35388 | | 12/1995 |
| WO | WO 96/21725 | | 7/1996 |
| WO | WO 97/05261 | | 2/1997 |
| WO | WO 97/08330 | | 3/1997 |
| WO | WO 97/12046 | | 4/1997 |
| WO | WO 97/32016 | | 9/1997 |
| WO | WO 97/41892 | | 11/1997 |
| WO | WO 97/44450 | | 11/1997 |
| WO | WO 97/49727 | | 12/1997 |
| WO | WO 98/05757 | | 2/1998 |
| WO | WO 98/30701 | | 7/1998 |
| WO | WO 98/32843 | | 7/1998 |
| WO | WO 99/10512 | | 3/1999 |
| WO | WO 99/14348 | | 3/1999 |
| WO | WO 99/25854 | | 5/1999 |
| WO | WO 99/32619 | | 7/1999 |
| WO | WO 99/32642 | | 7/1999 |
| WO | WO 99/49029 | | 9/1999 |
| WO | WO 99/53050 | | 10/1999 |
| WO | WO 99/61631 | | 12/1999 |
| WO | WO 00/12735 | | 3/2000 |
| WO | WO 00/18939 | | 4/2000 |
| WO | WO 00/29566 | | 5/2000 |
| WO | WO 00/37060 | | 6/2000 |
| WO | WO 00/37663 | | 6/2000 |
| WO | WO 00/63398 | | 10/2000 |
| WO | WO 00/67558 | | 11/2000 |
| WO | WO 01/09302 | | 2/2001 |
| WO | WO 01/38514 | | 5/2001 |
| WO | WO 01/44482 | | 6/2001 |
| WO | WO 01/49844 | | 7/2001 |
| WO | WO 01/51630 A1 | | 7/2001 |
| WO | WO 01/68836 A2 | | 9/2001 |
| WO | WO 01/77350 A2 | | 10/2001 |
| WO | WO 02/00927 | | 1/2002 |

OTHER PUBLICATIONS

Bevan & Flavell, "A Chimaeric Antibiotic Resistance Gene as a Selectable Marker for Plant Cell Transformation", Nature, 304: 184–187 (1983).

Chilton et al., "Tailoring the Agrobacterium Ti Plasmid as a Vector for Plant Genetic Engineering", Stadler Symp., 13: 39–53 (1981).

Colbere–Garapin et al., "A New Dominant Hybrid Selective Marker for Higher Eukaryotic Cells", J. Mol. Biol., 150: 1–14 (1981).

Davies and Jimenez, "A New Selective Agent for Eukaryotic Cloning Vectors", Am. J. Trop. Med. Hyg., 29(5): 1089–1092 (1980).

Depicker et al., "Nopaline Synthase: Transcript Mapping and DNA Sequence", Journal of Molecular and Applied Genetics, 1(6): 561–573 (1982).

Fraley et al., "Expression of Bacterial Genes in Plant Cells", Proc. Natl. Acad. Sci. USA, 80: 4803–4807 (1983).

Fraley et al., "Use of a Chimeric Gene to Confer Antibiotic Resistance to Plant Cells", Advances in Gene Technology: Molecular Genetics of Plants and Animals, 20: 211–221 (1983).

Framond et al., "Mini–Ti: A New Vector Strategy for Plant Genetic Engineering", BIO/TECHNOLOGY, 5: 262–269 (1983).

Hermaisteens et al., "The Agrobacterium Tumefaciens Ti Plasmid as a Host Vector System for Introducing Foreign DNA in Plant Cells", Nature, 287: 654–656 (1980).

Herrera–Estrella et al., "Chimeric Genes as Dominant Selectable Markers in Plant Cells", The Embo Journal, 2(6): 987–995 (1993).

Herrera–Estrella et al., "Expression of Chimaeric Genes Transferred into Plant Cells Using a Ti–Plasmid–Derived Vector", Nature, 303: 209–213 (1983).

Hooykaas et al., "The Ti–Plasmid of Agrobacterium Tumefaciens: A Nature Genetic Engineer", TIBS,307–309 (1985).

Horsch et al., "A Simple and General Method for Transferring Genes into Plants", Biological Sciences, 227: 1229–1231 (1985).

Lorz et al., "Transformation Studies Using Synthetic DNA Vectors Coding For Antibiotic Resistance", Plant Tissue Culture, 511–512 (1982).

Smith et al., "Antisense RNA Inhibition of Polygalacturonase Gene Expression in Transgenic Tomatoes", Nature, 334: 724–726 (1988).

Wang et al., "Right 25 bp Terminus Sequence of the Nopaline T—DNA is Essential for and Determines Direction of DNA transfer from Agrobacterium to the Plant Genome", Cell, 38: 455–462 (1984).

Database entry of Ensembl Human Genome Server, AC006461.2.1.181215, BLASTN 2.0a13MP–WashU [Jun. 10, 1997], 2 pp.

Database entry of Ensembl Human Genome Server, AC024028.10.1.176278, BLASTN 2.0a13MP–WashU [Jun. 10, 1997], 3 pp.

Database entry of Ensembl Human Genome Server, AC069205.6.1.132242, BLASTN 2.0a13MP–WashU [Jun. 10, 1997], 1 pp.

Database entry of Ensembl Human Genome Server, AC097498.3.1.144511, BLASTN 2.0a13Mp–WashU [Jun. 10, 1997], 1 pp.

Database entry of Ensembl Human Genome Server, AC104785.4.111369.213599, BLASTN 2.0a13MP–WashU [Jun. 10, 1997], 1 pp.

Database entry of Ensembl Human Genome Server, AC105416.3.1.123331, BLASTN 2.0a13MP–WashU [Jun. 10, 1997], 1 pp.

Database entry of Ensembl Human Genome Server, AC108146.3.1.91810, BLASTN 2.0a13MP–WashU [Jun. 10, 1997], 1 pp.

Database entry of Ensembl Human Genome Server, AC115109.2.1.59356, BLASTN 2.0a13MP–WashU [Jun. 10, 1997], 1 pp.

Genbank entry U27809. Peanut bud necrosis virus S segment non–structural protein and nucleocapsid protein genes, Jul. 23, 1996, 3 pp.

The Sanger Centre, "Toward a Complete Human Genome Sequence", Cold Spring Harbor Laboratory Press, 1097–1108, (1988).

Satyanarayana et al., "Peanut Bud Necrosis Tospovirus S RNA : Complete Nucleotide Sequence, Genome Organization and Homology to Other Tospoviruses", Arch. Virol. 141 (1), 85–98 (1996).

Genbank entry AB005879. Nicotania tabacum mRNA for BYJ6, Feb. 5, 1999, 2pp.

Genbank entry AC002131. Arabidopsis thaliana chromosome 1 BAC F12F1 sequence, May 28, 1998, 38 pp.

Genbank entry AC006461. Homo sapiens BAC clone RP11–343N14 from 2, Mar. 1, 2002, 65 pp.

Genbank entry AC024028. Homo sapiens BAC clone RP11–151M24 from 7, Nov. 7, 2001, 68 pp.

Genbank entry AC069205. Homo sapiens BAC clone RP11–735P12 from 2, Jan. 9, 2002, 46 pp.

Genbank entry AC079141. Homo sapiens BAC clone RP11–502A23 from 4, Nov. 7, 2001, 43 pp.

Genbank entry AC097498. Homo sapiens BAC clone RP11–326N15 from 4, Mar. 1, 2002, 51pp.

Genbank entry AC105416. Homo sapiens BAC clone RP11–310A13 from 4, Jun. 12, 2002, 47 pp.

Genbank entry AC108146. Homo sapiens BAC clone RP11–437H3 from 2, Mar. 9, 2002, 32 pp.

Genbank entry AC115109. Homo sapiens BAC clone RP11–78I10 from 2, May 29, 2002, 23 pp.

Genbank entry AR164048. Sequence 7 from patent U.S. 6271031, Oct. 17, 2001, 1 pp.

Genbank entry AR164050. Sequence 11 from patent U.S. 6271031, Oct. 17, 2001, 1pp.

Genbank entry AX344860. Sequence 285 from patent U.S. WO0200927, Feb. 1, 2002, 4pp.

Imanishi et al., "Differential Induction by Methyl Jasmonate of Genes Encoding Ornithine Decarboxylase and Other Enzymes Involved in Nicotine Biosynthesis in Tobacco Cell Cultures", Plant Molecular Biology, 38: 1101–1111 (1998).

Theologis et al., "Sequence and Analysis of Chromosome 1 of the Plant Arabidopsis Thaliana", Nature, 408: 816–820 (2000).

Hughes, Kelly T., et al., *The Salmonella typhimurium nadC Gene*: Sequence Determination by Use of Mud–P22 and Purification of Quinolinate Phosphoribosyltransferase, *Journal of Bacteriology*, vol. 175, No. 2, pp. 479–486 (Jan. 1993).

Wagner, Roland, et al., Determination of Quinolinic Acid Phosphoribosyl–Transferase in Tobacco, *Phytochemistry*, vol. 23, No. 9, pp. 1881–1883 (1884).

Conkling et al.; Isolation of transcriptionally regulated root–specific genes from tobacco; *Plant Physiology*; 93(3):1203–1211 (1990).

Song, Wen; Molecular characterizations of two tobacco root–specific genes: TobRB7 and NtQPTl; (1997) 224 PP. Avail: UMI, Order No. DA9804246 from: Diss. Abstr. Int., B 1998, 58(8), 4061 XP002080228.

Hamill et al.; Over–expressing a yeast ornithine decarboxylase gene in transgenic roots of *Nicotiana rustica* can lead to enhanced nicotine accumulation; *Plant Molecular Biology* 15:27–38 (1990).

Holmberg et al.; Transgenic tobacco expressing *Vitreoscilla hemoglobin* exhibits enhanced growth and altered metabolite production, *Nature Biotechnology* 15:244–247 (1997).

Copy of International Search report—date of mailing Oct. 22, 1998.

Burtin D. and Michael, A.J., "Over expression of Arginine Decarboxylase in Transgenic Plants", *Biochem J.* 325 (part 2) 331–337 (1997).

Bush and Saunders, Physiological Aspects of Genetic Variation in Nicotine Content in Tobacco (*Nicotiana tabacum*):, *Tobacco Abstract*, 23, p. 380 (1979).

Bush and Saunders, "Nicotine Biosynthetic Enzymes of Burley Tobacco", *Tobacco Abstracts*, 24, p. 260 (1980).

Cornelissen and Vandewiele, "Both RNA Level and Translation Efficiency Are Reduced by Anti–Sense RNA In Transgenic tobacco", *Nucleic Acids Res.*, 17, 3, pp. 833–843 (1989).

Crowley et al., *Cell* 43:633–641 (1985).

Cuozzo et al., Viral Protection in Transgenic Tobacco Plants Expressing The Cucumber Mosaic VirusCoat Protein Or Its Antisense RNA:, *Biotechnology*, 6:549–557 (1988).

Delauney et al., A Stable Bifunctional Antisense Transcript Inhibiting Gene Expression In Transgenic Plants:, *Proc. Natl. Acad. Sci. USA*, 85:4300–4304 (1988).

Ecker and Davis, "Inhibition Of Gene Expression In Plant Cells by Expression of Antisense RNA", *Proc. Natl. Acad. Sci. USA*, 83:5372–5376 (1986).

Feth et al., "Regulation in Tobacco Callus or Enzyme Activities of the Nicotine Pathway", *Planta*, 168:402–407.

Hemenway et al., "Analysis of the Mechanism of Protection In Transgenic Plants Expressing The Potato Virus x Coat Protein Or its Antisense RNA", *EMBO J.*, 7:1273–1280.

Hibi et al., "Gene Expression in Tobacco Low–Nicotine Mutants", *Plant Cell* 6 723–35 (1994).

Izant and Weintraub, "Constitutive and Conditional Suppression of Exogenous and Endogenous Genes by Anti–Sense RNA", *Science*, 229:345–352 (1985).

Izant and Weintraub, "Inhibition of Thymidine Kinase Gene Expression by Anti–Sense RNA: A Molecular Approach to Genetic Analysis", *Cell*, 36: 1007–1015, Apr. 1984.

Kim and Wold, "Stable Reduction of Thymidine Kinase Activity in Cells Expressing High Levels of Anti–Sense RNA", *Cell*, 42:129–138 (Aug. 1985).

Lam et al., "Site–Specific Mutations Alter in Vitro Factor Binding and Change Promoter Expression Pattern in Transgenic Plants", *Proc. Nat. Acad. Sci. USA* 86:7890–7894 (1989).
Lichtenstein, "Anti–sense RNA As A Tool To Study Plant Gene Expression", *Nature*, 333:801–802 (1988).
McGarry and Lindquist, *Proc.Natl. Acad. Sci. USA* (*1986*).
Melton, "Injected Anti–Sense RNAs Specifically Block Messenger RNA Translation In Vivo", *Proc. Natl. Acad. Sci. USA*, 82:144–148 (1985).
Mizuno et al. "A Unique Mechanism Regulating Gene Expression: Translational Inhibition By a Complementary RNA Transcript (micRNA)", *Trends in Genetics*, 1:22–25 (1985).
Ohta and Yatazawa, "Metabolic Key Step Discriminating Nicotine Producing Tobacco Callus Strain From Ineffective One", *Biochem. Physiol. Pflanzen*, 175: 382–385 (1980).
Pestka et al. "Anti–mRNA: Specific Inhibition Of Translation Of Single mRNA Molecules", *Proc. Natl. Acad. Sci. USA*, 81:7525–7528 (1984).
Poulsen et al., "Dissection of 5' Upstream Sequences For Selective Expression Of The Nicotiana Plumbaginifolia rbsS–8B gene", *Mol. Gen. Genet.*, 214:16–23 (1988).
Preiss et al., "Molecular Genetics of Krüppel, A Gene Required for Segmentation Of The Drosophila Embryo", *Nature*, 313:27–32 (1985).
Rezaian et al., "Anti–Sense RNAs of Cucumber Mosaic Virus in Transgenic Plants Assessed For Control Of The Virus", *Plant Molecular Biology*, 11:463–471 (1988).
Rodermel et al, "Nuclear–Organelle Interactions: Nuclear Antisense Gene Inhibits Ribulose Bisphosphate Carboxylase Enzyme Levels In Transformed Tobacco Plants", *Cell*, 55:673–681 (1988).
Rosenberg et al., Production Of Phenocopies By Krüppel Antisense RNA Injection Into Drosophila Embryos, *Nature*, 313:703–706 (1985).
Rothstein et al., "Stable and Heritable Inhibition Of The Expression Of nopaline synthase In Tobacco Expressing Antisense RNA", *Proc. Natl. Sci. USA*, 84:8439–8443 (1987).
Sandler et al., "Inhibition of Gene Expression In Transformed plants by antisense RNA", *Plant Molecular Biology*, 11:301–310 (1988).
Saunders and Bush, Comparison of Nicotine Biosynthetic Enzymes in Nicotine Level Genotypes of Burley Tobacco:, *Agronomy Abstracts*, p. 84 (1978).
Saunders and Bush, "Enzyme Activities in Nicotine Biosynthesis In Nicotiana Tabacum", *Journal of Natural Products*, 41, p. 646.
Sheehy et al., Reduction of Polygalacturonase Activity In Tomato Fruit by Antisense RNA:, *Proc. Natl. Acad. Sci. USA*, 85:8805–8809 (1988).
Smith et al., "Antisense RNA Inhibition of Polygalacturonase Gene Expression In Transgenci Tomatoes", *Nature*, 334:724–726 (1988).
Travers, "Regulation by Anti–Sense RNA", *Nature*, 310, p. 410 (1984).
Van der Krol et al., "An Anti–Sense Chalcone Synthase Gene In Transgenic Plants Inhibits Flower Pigmentation", *Nature*, 333:866–869 (1988).
Van der Krol et al., "Modulation of Eukaryotic Gene Expression by Complementary RNA Or DNA Sequences", *Biotechniques*, 6:958–976 (1988).
Van der Kroll et al., "Antisense Genes In Plants; An Overview", *Gene*, 72:45–50 (1988).
Wagner et al., "The Regulation of Enzyme Activities of the Nicotine Pathway In Tobacco", *Physiol. Plantarum*, 68:667–672 (1986).
Wagner et al., Regulation in Tobacco Callus of Enzyme Activities of the Nicotine Pathway:, *Planta*, 168, 408–412.
Weintraub, et al., "Anti–sense RNA as a Molecular Tool for Genetic Analysis", *Trends in Genetics*, 1:22–25 (1985).
West et al., "Duplex–Duplex Interactions Catalyzed by RecA Protein Allow Strand Exchanges to Pass Double–Strand Breaks in DNA", *Cell*, 37 683–691 (1984).

* cited by examiner

```
caaaaactat tttccacaaa attcatttca caacccccc aaaaaaaaac cATGTTTAGA   60
GCTATTCCTT TCACTGCTAC AGTGCATCCT TATGCAATTA CAGCTCCAAG GTTGGTGGTG  120
AAAATGTCAG CAATAGCCAC CAAGAATACA AGAGTGGAGT CATTAGAGGT GAAACCACCA  180
GCACACCCAA CTTATGATTT AAAGGAAGTT ATGAAACTTG CACTCTCTGA AGATGCTGGG  240
TTTCTAGCAA AGGAAGACGG GATCATAGCA GGAATTGCAC TTGCTGAGAT GATATTCGCG  360
GAAGTTGATC CTTCATTAAA GGTGGAGTGG TATGTAAATG ATGGCGATAA AGTTCATAAA  420
GGCTTGAAAT TTGGCAAAGT ACAAGGAAAC GCTTACAACA TTGTTATAGC TGAGAGGGTT  480
GTTCTCAATT TTATGCAAAG AATGAGTGGA ATAGCTACAC TAACTAAGGA AATGGCAGAT  540
GCTGCACACC CTGCTTACAT CTTGGAGACT AGGAAAACTG CTCCTGGATT ACGTTTGGTG  600
GATAAATGGG CGGTATTGAT CGGTGGGGGG AAGAATCACA GAATGGGCTT ATTTGATATG  660
GTAATGATAA AAGACAATCA CATATCTGCT GCTGGAGGTG TCGGCAAAGC TCTAAAATCT  720
GTGGATCAGT ATTTGGAGCA AAATAAACTT CAAATAGGGG TTGAGGTTGA AACCAGGACA  780
ATTGAAGAAG TACGTGAGGT TCTAGACTAT GCATCTCAAA CAAAGACTTC GTTGACTAGG  840
ATAATGCTGG ACAATATGGT TGTTCCATTA TCTAACGGAG ATATTGATGT ATCCATGCTT  900
AAGGAGGCTG TAGAATTGAT CAATGGGAGG TTTGATACGG AGGCTTCAGG AAATGTTACC  960
CTTGAAACAG TACACAAGAT TGGACAAACT GGTGTTACCT ACATTTCTAG TGGTGCCCTG 1020
ACGCATTCCG TGAAAGCACT TGACATTTCC CTGAAGATCG ATACAGAGCT CGCCCTTGAA 1080
GTTGGAAGGC GTACAAAACG AGCATGAgcg ccattacttc tgctataggg ttggagtaaa 1140
agcagctgaa tagctgaaag gtgcaaataa gaatcatttt actagttgtc aaacaaaaga 1200
tccttcactg tgtaatcaaa caaaaagatg taaattgctg gaatatctca gatggctctt 1260
ttccaacctt attgcttgag ttggtaattt cattatagct ttgttttcat gtttcatgga 1320
atttgttaca atgaaaatac ttgatttata agtttggtgt atgtaaaatt ctgtgttact 1380
tcaaatattt tgagatgtt                                              1399
```

FIGURE 2A

```
MFRAIPFTAT VHPYAITAPR LVVKMSAIAT KNTRVESLEV KPPAHPTYDL   50
KEVMKLALSE DAGNLGDVTC KATIPLDMES DAHFLAKEDG IIAGIALAEM  100
IFAEVDPSLK VEWYVNDGDK VHKGLKFGKV QGNAYNIVIA ERVVLNFMQR  150
MSGIATLTKE MADAAHPAYI LETRKTAPGL RLVDKWAVLI GGGKNHRMGL  200
FDMVMIKDNH ISAAGGVGKA LKSVDQYLEQ NKLQIGVEVE TRTIEEVREV  250
LDYASQTKTS LTRIMLDNMV VPLSNGDIDV SMLKEAVELI NGRFDTEASG  300
NVTLETVHKI GQTGVTYISS GALTHSVKAL DISLKIDTEL ALEVGRRTKR  350
A                                                       351
```

FIGURE 2B

| | |
|---|---|
| N. tabacum | MFRAIPFTATVHPYAITAPRLVVKMSAIATKNTRVESLEVKPPAHPTYDL |
| R. rubrum | *--------RPNH-----------------------PVAALS*F----AI |
| M. leprae | *--------LSDC-----------------------EFDAAR-------- |
| S. typhimurium | *--------PPRR*NPDDR*-----------DALL*RINLDI*A----AV |
| E. coli | *--------PPRR*NPDTR*-----------DELL*RINLDI*G----AV |
| H. sapien | *---------------D*EG*ALLLPPVTLAALVDSWLREDC*G------ |
| S. cerevisiae | *---------------PVYE-HLLPVNGAWRQDVTNWLSEDV*S------ |

| | |
|---|---|
| N. tabacum | KEVMKLALSEDAGNLGDVTCKATIPLDMESDAHFLAKEDGIIAGIA---- |
| R. rubrum | D*AVRR**A**L*RA**I*ST****AATRAH*RFV*RQP**L**LGCA-- |
| M. leprae | -DTIRR**H**LRYGL*I*TQ**V*AGTVVTGSMVPR*P*VIAGVDVALL |
| S. typhimurium | AQALREDLGGEVDAGN*I*AQL-L*A*TQAH*TVITR*D*VF----CGKR |
| E. coli | AQALREDLGGTVDANN*I*A*L-L*ENSR*H*TVITR*N*VF----CGKR |
| H. sapien | -----------------LNYAALVSGAGP*QAALWAKSP*VL----AGQP |
| S. cerevisiae | -----------------FDFGGYVVGSDLKEANLYCKQD*ML----CGVP |

| | |
|---|---|
| N. tabacum | -LAEMIFAEVDPSLKVEWYVNDGDKVHKGLK------FGKVQGNAYNIVI |
| R. rubrum | --RSAF-ALLDDTVTFTTPLE**AEIAA*QT------VAE*A*A*RT*LA |
| M. leprae | VLD*VF-GVDGYRVLY--R*E**ARLQS*QP------LLTVQAA*RGLLT |
| S. typhimurium | WVE*VFIQLAGDDVRLT*H*D***AI*ANQT------VFELN*PARVLLT |
| E. coli | WVE*VFIQLAGDDVTII*H*D***VINANQS------LFELE*PSRVLLT |
| H. sapien | FFDAIFTQL---NCQVS*FLPE*S*LVPVAR------VAEVR*P*HDLLL |
| S. cerevisiae | FAW*VFNQC---ELQVE*LFKE*SFLEPSKNDSGKIVVAKIT*P*K**LL |

| | |
|---|---|
| N. tabacum | AERVVLNFMQRMSGIATLTKEMAD--AAH--PAYILETRKTAPGLRLVDK |
| R. rubrum | ***TA***LGHL*****R*RRFG*AI*HT--R*RLTC****T****GLE* |
| M. leprae | ***TM***VCHM*****V*VAWV*AVRGT--K*KIRD****L****ALQ* |
| S. typhimurium | G**TA***V*TL**VASEVRRYVGLL*GT--QTQL*D****L****TAL* |
| E. coli | G*PTA***V*TL**VASKVRHYVELLEGT--NTQL*D****L****SAL* |
| H. sapien | G***A**TLARC****SAAAAAVEAARGAGWTGHVAG****T**F***E* |
| S. cerevisiae | ***TA**ILSRS****TASHKIISLARSTGYKGTIAG****T****RLE* |

| | |
|---|---|
| N. tabacum | WAVLIGGGKNHRMGLFDMVMIKDNHISAAGGVGKALKSVDQYLEQNKLQI |
| R. rubrum | Y**RC***S***F**D*A*L******AVA***SA**SRAR-AGVGHMVRI |
| M. leprae | Y**RV***V***L**G*TAL*****VA*V*S*VD**RA*R-AAAPEL-PC |
| S. typhimurium | Y***C***A***L**T*AFL******I*S*S*RQ*VEKAF-W*HPD-APV |
| E. coli | Y***C***A***L**S*AFL******I*S*S*RQ*VEKAS-W*HPD-APV |
| H. sapien | YGL*V**AAS**YD*GGLVML*D**VVPP***EK*VRAARQ---AADFAL |
| S. cerevisiae | YSM*V**CDT**YD*SS**ML*D***W*T*SITN*V*NARA---VCGFAV |

FIGURE 3

| | |
|---|---|
| N. tabacum | GVEVETRTIEEVREVLDYASQTKTSLTRIMLDNMVVPLSNGDIDVSMLKE |
| R. rubrum | EI****--L*QLA***AVGGAEV-----VL****-----DAPT----*TR |
| M. leprae | E****S--L*QLDAM*A-EEPEL-----*L***F--*VWQTQV----AVQ |
| S. typhimurium | E****N--LDELDDA*K-*GADI-----*****F-----NTDQ----MR* |
| E. coli | E****N--L**LD*A*K-*GADI-----*****F-----ETEQ----MR* |
| H. sapien | K****CSSLQ**VQAAE-*GADL-----VL***F------KPEELHPTAT |
| S. cerevisiae | KI***CLSED*AT*AIE-*GADV-----*****F------KGDGLK*CAQ |

| | |
|---|---|
| N. tabacum | AVELI---NGRFDTEASGNVTLETVHKIG-QTGVTYISSGALTHSVKALD |
| R. rubrum | **DMV---A**LV*****G*S*D*IAALA-ES**D***V*******TT** |
| M. leprae | RRDIR---APTVLL*S**GLS**NAAIYA-G***DYLAV*******RI** |
| S. typhimurium | **KRV---**QARL*V*****AE*LREFA-E***DF**VG******R*** |
| E. coli | **KRT---**KALL*V*****DK*LREFA-E***DF**V*******Q*** |
| H. sapien | *LKAQFPSVA---VEA**GIT*DNLPQF-CGPHIDV**M*M**QA*P*** |
| S. cerevisiae | SLKNKWNGKKHFLLEC**GLN*DNLEEYLCD-DIDIY*TSSIHQGTPVI* |

| | | % Identity | % Similarity |
|---|---|---|---|
| N. tabacum | ISKLIDTELALEVGRRTKRA | | |
| R. rubrum | *G*D*VVA-----PPKAERA | 15.9 | 43.2 |
| M. leprae | *G*DL | 18.3 | 37.3 |
| S. typhimurium | LSMRFC | 18.2 | 34.8 |
| E. coli | LSMRFR | 17.9 | 32.8 |
| H. sapien | F***L---F*K*VAPVP*IH | 16.8 | 31.7 |
| S. cerevisiae | F***LAH | 14.6 | 27.8 |

FIGURE 3 continued

SEQUENCE LISTING

```
<160> NUMBER OF SEQ ID NOS: 3

<210> SEQ ID NO 1
<211> LENGTH: 1399
<212> TYPE: DNA
<213> ORGANISM: Nicotiana tabacum
<220> FEATURE:
<221> NAME/KEY: CDS
<222> LOCATION: (52)..(1104)

<400> SEQUENCE: 1

caaaaactat tttccacaaa attcatttca caaccccccc aaaaaaaaac c atg ttt      57
                                                         Met Phe
                                                           1

aga gct att cct ttc act gct aca gtg cat cct tat gca att aca gct      105
Arg Ala Ile Pro Phe Thr Ala Thr Val His Pro Tyr Ala Ile Thr Ala
        5                   10                  15

cca agg ttg gtg gtg aaa atg tca gca ata gcc acc aag aat aca aga      153
Pro Arg Leu Val Val Lys Met Ser Ala Ile Ala Thr Lys Asn Thr Arg
    20                  25                  30

gtg gag tca tta gag gtg aaa cca cca gca cac cca act tat gat tta      201
Val Glu Ser Leu Glu Val Lys Pro Pro Ala His Pro Thr Tyr Asp Leu
 35                  40                  45                  50

aag gaa gtt atg aaa ctt gca ctc tct gaa gat gct ggg aat tta gga      249
Lys Glu Val Met Lys Leu Ala Leu Ser Glu Asp Ala Gly Asn Leu Gly
                 55                  60                  65

gat gtg act tgt aag gcg aca att cct ctt gat atg gaa tcc gat gct      297
Asp Val Thr Cys Lys Ala Thr Ile Pro Leu Asp Met Glu Ser Asp Ala
            70                  75                  80

cat ttt cta gca aag gaa gac ggg atc ata gca gga att gca ctt gct      345
His Phe Leu Ala Lys Glu Asp Gly Ile Ile Ala Gly Ile Ala Leu Ala
        85                  90                  95

gag atg ata ttc gcg gaa gtt gat cct tca tta aag gtg gag tgg tat      393
Glu Met Ile Phe Ala Glu Val Asp Pro Ser Leu Lys Val Glu Trp Tyr
    100                 105                 110

gta aat gat ggc gat aaa gtt cat aaa ggc ttg aaa ttt ggc aaa gta      441
Val Asn Asp Gly Asp Lys Val His Lys Gly Leu Lys Phe Gly Lys Val
115                 120                 125                 130

caa gga aac gct tac aac att gtt ata gct gag agg gtt gtt ctc aat      489
Gln Gly Asn Ala Tyr Asn Ile Val Ile Ala Glu Arg Val Val Leu Asn
                135                 140                 145

ttt atg caa aga atg agt gga ata gct aca cta act aag gaa atg gca      537
Phe Met Gln Arg Met Ser Gly Ile Ala Thr Leu Thr Lys Glu Met Ala
            150                 155                 160

gat gct gca cac cct gct tac atc ttg gag act agg aaa act gct cct      585
Asp Ala Ala His Pro Ala Tyr Ile Leu Glu Thr Arg Lys Thr Ala Pro
        165                 170                 175

gga tta cgt ttg gtg gat aaa tgg gcg gta ttg atc ggt ggg ggg aag      633
Gly Leu Arg Leu Val Asp Lys Trp Ala Val Leu Ile Gly Gly Gly Lys
    180                 185                 190

aat cac aga atg ggc tta ttt gat atg gta atg ata aaa gac aat cac      681
Asn His Arg Met Gly Leu Phe Asp Met Val Met Ile Lys Asp Asn His
195                 200                 205                 210

ata tct gct gct gga ggt gtc ggc aaa gct cta aaa tct gtg gat cag      729
Ile Ser Ala Ala Gly Gly Val Gly Lys Ala Leu Lys Ser Val Asp Gln
                215                 220                 225

tat ttg gag caa aat aaa ctt caa ata ggg gtt gag gtt gaa acc agg      777
Tyr Leu Glu Gln Asn Lys Leu Gln Ile Gly Val Glu Val Glu Thr Arg
            230                 235                 240
```

-continued

```
aca att gaa gaa gta cgt gag gtt cta gac tat gca tct caa aca aag      825
Thr Ile Glu Glu Val Arg Glu Val Leu Asp Tyr Ala Ser Gln Thr Lys
        245                 250                 255

act tcg ttg act agg ata atg ctg gac aat atg gtt gtt cca tta tct      873
Thr Ser Leu Thr Arg Ile Met Leu Asp Asn Met Val Val Pro Leu Ser
    260                 265                 270

aac gga gat att gat gta tcc atg ctt aag gag gct gta gaa ttg atc      921
Asn Gly Asp Ile Asp Val Ser Met Leu Lys Glu Ala Val Glu Leu Ile
275                 280                 285                 290

aat ggg agg ttt gat acg gag gct tca gga aat gtt acc ctt gaa aca      969
Asn Gly Arg Phe Asp Thr Glu Ala Ser Gly Asn Val Thr Leu Glu Thr
                295                 300                 305

gta cac aag att gga caa act ggt gtt acc tac att tct agt ggt gcc     1017
Val His Lys Ile Gly Gln Thr Gly Val Thr Tyr Ile Ser Ser Gly Ala
            310                 315                 320

ctg acg cat tcc gtg aaa gca ctt gac att tcc ctg aag atc gat aca     1065
Leu Thr His Ser Val Lys Ala Leu Asp Ile Ser Leu Lys Ile Asp Thr
        325                 330                 335

gag ctc gcc ctt gaa gtt gga agg cgt aca aaa cga gca tgagcgccat      1114
Glu Leu Ala Leu Glu Val Gly Arg Arg Thr Lys Arg Ala
    340                 345                 350

tacttctgct atagggttgg agtaaaagca gctgaatagc tgaaaggtgc aaataagaat   1174

cattttacta gttgtcaaac aaaagatcct tcactgtgta atcaaacaaa aagatgtaaa   1234

ttgctggaat atctcagatg gctcttttcc aaccttattg cttgagttgg taatttcatt   1294

atagctttgt tttcatgttt catggaattt gttacaatga aaatacttga tttataagtt   1354

tggtgtatgt aaaattctgt gttacttcaa atattttgag atgtt                   1399


<210> SEQ ID NO 2
<211> LENGTH: 351
<212> TYPE: PRT
<213> ORGANISM: Nicotiana tabacum

<400> SEQUENCE: 2

Met Phe Arg Ala Ile Pro Phe Thr Ala Thr Val His Pro Tyr Ala Ile
  1               5                  10                  15

Thr Ala Pro Arg Leu Val Val Lys Met Ser Ala Ile Ala Thr Lys Asn
            20                  25                  30

Thr Arg Val Glu Ser Leu Glu Val Lys Pro Pro Ala His Pro Thr Tyr
        35                  40                  45

Asp Leu Lys Glu Val Met Lys Leu Ala Leu Ser Glu Asp Ala Gly Asn
     50                  55                  60

Leu Gly Asp Val Thr Cys Lys Ala Thr Ile Pro Leu Asp Met Glu Ser
 65                  70                  75                  80

Asp Ala His Phe Leu Ala Lys Glu Asp Gly Ile Ile Ala Gly Ile Ala
                85                  90                  95

Leu Ala Glu Met Ile Phe Ala Glu Val Asp Pro Ser Leu Lys Val Glu
            100                 105                 110

Trp Tyr Val Asn Asp Gly Asp Lys Val His Lys Gly Leu Lys Phe Gly
        115                 120                 125

Lys Val Gln Gly Asn Ala Tyr Asn Ile Val Ile Ala Glu Arg Val Val
    130                 135                 140

Leu Asn Phe Met Gln Arg Met Ser Gly Ile Ala Thr Leu Thr Lys Glu
145                 150                 155                 160

Met Ala Asp Ala Ala His Pro Ala Tyr Ile Leu Glu Thr Arg Lys Thr
                165                 170                 175
```

-continued

```
Ala Pro Gly Leu Arg Leu Val Asp Lys Trp Ala Val Leu Ile Gly Gly
            180                 185                 190

Gly Lys Asn His Arg Met Gly Leu Phe Asp Met Val Met Ile Lys Asp
        195                 200                 205

Asn His Ile Ser Ala Ala Gly Gly Val Gly Lys Ala Leu Lys Ser Val
    210                 215                 220

Asp Gln Tyr Leu Glu Gln Asn Lys Leu Gln Ile Gly Val Glu Val Glu
225                 230                 235                 240

Thr Arg Thr Ile Glu Glu Val Arg Glu Val Leu Asp Tyr Ala Ser Gln
                245                 250                 255

Thr Lys Thr Ser Leu Thr Arg Ile Met Leu Asp Asn Met Val Val Pro
            260                 265                 270

Leu Ser Asn Gly Asp Ile Asp Val Ser Met Leu Lys Glu Ala Val Glu
        275                 280                 285

Leu Ile Asn Gly Arg Phe Asp Thr Glu Ala Ser Gly Asn Val Thr Leu
    290                 295                 300

Glu Thr Val His Lys Ile Gly Gln Thr Gly Val Thr Tyr Ile Ser Ser
305                 310                 315                 320

Gly Ala Leu Thr His Ser Val Lys Ala Leu Asp Ile Ser Leu Lys Ile
                325                 330                 335

Asp Thr Glu Leu Ala Leu Glu Val Gly Arg Arg Thr Lys Arg Ala
            340                 345                 350


<210> SEQ ID NO 3
<211> LENGTH: 1053
<212> TYPE: DNA
<213> ORGANISM: Nicotiana tabacum

<400> SEQUENCE: 3

atgtttagag ctattccttt cactgctaca gtgcatcctt atgcaattac agctccaagg     60

ttggtggtga aaatgtcagc aatagccacc aagaatacaa gagtggagtc attagaggtg    120

aaaccaccag cacacccaac ttatgattta aaggaagtta tgaaacttgc actctctgaa    180

gatgctggga atttaggaga tgtgacttgt aaggcgacaa ttcctcttga tatggaatcc    240

gatgctcatt ttctagcaaa ggaagacggg atcatagcag gaattgcact tgctgagatg    300

atattcgcgg aagttgatcc ttcattaaag gtggagtggt atgtaaatga tggcgataaa    360

gttcataaag gcttgaaatt tggcaaagta caaggaaacg cttacaacat tgttatagct    420

gagagggttg ttctcaattt tatgcaaaga atgagtggaa tagctacact aactaaggaa    480

atggcagatg ctgcacaccc tgcttacatg ttggagacta ggaaaactgc tcctggatta    540

cgtttggtgg ataaatgggc ggtattgatc ggtggggga agaatcacag aatgggctta    600

tttgatatgg taatgataaa agacaatcac atatctgctg ctggaggtgt cggcaaagct    660

ctaaaatctg tggatcagta tttggagcaa aataaacttc aaatagggt tgaggttgaa    720

accaggacaa ttgaagaagt acgtgaggtt ctagactatg catctcaaac aaagacttcg    780

ttgactagga taatgctgga caatatggtt gttccattat ctaacggaga tattgatgta    840

tccatgctta aggaggctgt agaattgatc aatgggaggt ttgatacgga ggcttcagga    900

aatgttaccc ttgaaacagt acacaagatt ggacaaactg gtgttaccta catttctagt    960

ggtgccctga cgcattccgt gaaagcactt gacatttccc tgaagatcga tacagagctc   1020

gcccttgaag ttggaaggcg tacaaaacga gca                                1053
```

REGULATION OF QUINOLATE PHOSPHORIBOSYL TRANSFERASE EXPRESSION BY TRANSFORMATION WITH A TOBACCO QUINOLATE PHOSPHORIBOSYL TRANSFERASE NUCLEIC ACID

CROSS REFERENCE TO RELATED APPLICATION

This application claims the benefit of U.S. Provisional Application No. 60/049,471, filed Jun. 12, 1997.

FEDERALLY SPONSORED RESEARCH

This invention was made with Government support under National Science Foundation Grant No. MCB-9206506. The Government has certain rights to this invention.

FIELD OF THE INVENTION

This invention relates to plant quinolate phosphoribosyl transferase (QPRTase) and to DNA encoding this enzyme. In particular, this invention relates to the use of DNA encoding quinolate phosphoribosyl transferase to produce transgenic plants having genetically altered nicotine levels, and the plants so produced.

BACKGROUND OF THE INVENTION

The production of tobacco with decreased levels of nicotine is of interest, given concerns regarding the addictive nature of nicotine. Additionally, tobacco plants with extremely low levels of nicotine production, or no nicotine production, are attractive as recipients for transgenes expressing commercially valuable products such as pharmaceuticals, cosmetic components, or food additives. Various processes have been designed for the removal of nicotine from tobacco. However, most of these processes remove other ingredients from tobacco in addition to nicotine, thereby adversely affecting the tobacco. Classical crop breeding techniques have produced tobacco plants with lower levels of nicotine (approximately 8%) than that found in wild-type tobacco plants. Tobacco plants and tobacco having even further reductions in nicotine content are desirable.

One approach for reducing the level of a biological product is to reduce the amount of a required enzyme in the biosynthetic pathway leading to that product. Where the affected enzyme naturally occurs in a rate-limiting amount (relative to the other enzymes required in the pathway), any reduction in that enzyme's abundance will decrease the production of the end product. If the amount of the enzyme is not normally rate limiting, its presence in a cell must be reduced to rate-limiting levels in order to diminish the pathway's output. Conversely, if the naturally-occurring amount of enzyme is rate limiting, then any increase in the enzyme's activity will result in an increase in the biosynthetic pathway's end product.

Nicotine is formed primarily in the roots of the tobacco plant and is subsequently transported to the leaves, where it is stored (Tso, *Physiology and Biochemistry of Tobacco Plants*, pp. 233–34, Dowden, Hutchinson & Ross, Stroudsburg, Pa. (1972)). An obligatory step in nicotine biosynthesis is the formation of nicotinic acid from quinolinic acid, which step is catalyzed by the enzyme quinoline phosphoribosyl transferase ("QPRTase"). QPRTase appears to be a rate-limiting enzyme in the pathway supplying nicotinic acid for nicotine synthesis in tobacco. See, e.g., Feth et al., "Regulation in Tobacco Callus of Enzyme Activities of the Nicotine Pathway", *Planta*, 168, pp. 402–07 (1986); Wagner et al., "The Regulation of Enzyme Activities of the Nicotine Pathway in Tobacco", *Physiol. Plant.*, 68, pp. 667–72 (1986). The modification of nicotine levels in tobacco plants by antisense regulation of putrescence methyl transferase (PMTase) expression is proposed in U.S. Pat. Nos. 5,369,023 and 5,260,205 to Nakatani and Malik. PCT application WO 94/28142 to Wahad and Malik describes DNA encoding PMT and the use of sense and antisense PMT constructs.

SUMMARY OF THE INVENTION

A first aspect of the present invention is an isolated DNA molecule comprising SEQ ID NO:1; DNA sequences which encode an enzyme having SEQ ID NO:2; DNA sequences which hybridize to such DNA and which encode a quinolate phosphoribosyl transferase enzyme; and DNA sequences which differ from the above DNA due to the degeneracy of the genetic code. A peptide encoded by such DNA is a further aspect of the invention.

A further aspect of the present invention is a DNA construct comprising a promoter operable in a plant cell and a DNA segment encoding a quinolate phosphoribosyl transferase enzyme positioned downstream from the promoter and operatively associated therewith. The DNA encoding the enzyme may be in the antisense or sense direction.

A further aspect of the present invention is a method of making transgenic plant cell having reduced quinolate phosphoribosyl transferase (QPRTase) expression, by providing a plant cell of a type known to express quinolate phosphoribosyl transferase; transforming the plant cell with an exogenous DNA construct comprising a promoter and DNA comprising a portion of a sequence encoding quinolate phosphoribosyl transferase mRNA.

A further aspect of the present invention is a transgenic plant of the species Nicotiana having reduced quinolate phosphoribosyl transferase (QPRTase) expression relative to a non-transformed control plant. The cells of such plants comprise a DNA construct which includes a segment of a DNA sequence that encodes a plant quinolate phosphoribosyl transferase mRNA.

A further aspect of the present invention is a method for reducing expression of a quinolate phosphoribosyl transferase gene in a plant cell by growing a plant cell transformed to contain exogenous DNA, where a transcribed strand of the exogenous DNA is complementary to quinolate phosphoribosyl transferase mRNA endogenous to the cell. Transcription of the complementary strand reduces expression of the endogenous quinolate phosphoribosyl gene.

A further aspect of the present invention is a method of producing a tobacco plant having decreased levels of nicotine in leaves of the tobacco plant by growing a tobacco plant with cells that comprise an exogenous DNA sequence, where a transcribed strand of the exogenous DNA sequence is complementary to endogenous quinolate phosphoribosyl transferase messenger RNA in the cells.

A further aspect of the present invention is a method of making a transgenic plant cell having increased quinolate phosphoribosyl transferase (QPRTase) expression, by transforming a plant cell known to express quinolate phosphoribosyl transferase with an exogenous DNA construct which comprises a DNA sequence encoding quinolate phosphoribosyl transferase.

A further aspect of the present invention is a transgenic Nicotiana plant having increased quinolate phosphoribosyl transferase (QPRTase) expression, where cells of the transgenic plant comprise an exogenous DNA sequence encoding a plant quinolate phosphoribosyl transferase.

A further aspect of the present invention is a method for increasing expression of a quinolate phosphoribosyl transferase gene in a plant cell, by growing a plant cell transformed to contain exogenous DNA encoding quinolate phosphoribosyl transferase.

A further aspect of the present invention is a method of producing a tobacco plant having increased levels of nicotine in the leaves, by growing a tobacco plant having cells that contain an exogenous DNA sequence that encodes quinolate phosphoribosyl transferase functional in the cells.

BRIEF DESCRIPTION OF THE DRAWINGS

FIG. 2A provides the nucleic acid sequence of NtQPT1 cDNA (SEQ ID NO:1), with the coding sequence (SEQ ID NO:3) shown in capital letters.

FIG. 2B provides the deduced amino acid sequence (SEQ ID NO:2) of the tobacco QPRTase encoded by NtQPT1 cDNA.

FIG. 3 aligns the deduced NtQPT1 amino acid sequence and related sequences of *Rhodospirillum rubrun, Mycobacterium lepre, Salmonella typhimurium, Escherichia coli*, human, and *Saccharomyces cerevisiae.*

DETAILED DESCRIPTION OF THE INVENTION

Figure 1:
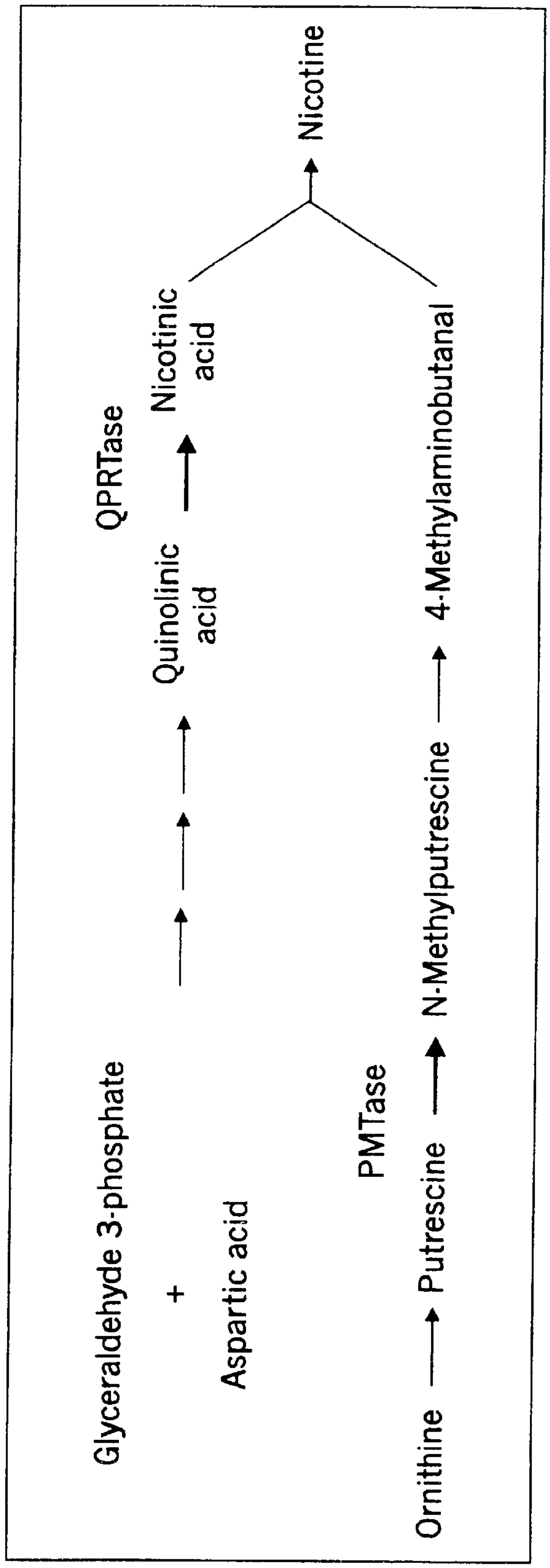
FIG. 1 shows the biosynthetic pathway leading to nicotine. Enzyme activities known to be regulated by Nic1 and Nic2 are QPRTase (quinolate phosphoribosyl transferase) and PMTase (putrescence methyltransferase).

Nicotine is produced in tobacco plants by the condensation of nicotinic acid and 4-methylaminobutanal. The biosynthetic pathway resulting in nicotine production is illustrated in FIG. 1. Two regulatory loci (Nic1 and Nic2) act as co-dominant regulators of nicotine production. Enzyme analyses of roots of single and double Nic mutants show that the activities of two enzymes, quinolate phosphoribosyl transferase (QPRTase) and putrescence methyl transferase (PMTase), are directly proportional to levels of nicotine biosynthesis. A comparison of enzyme activity in tobacco tissues (root and callus) with different capacities for nicotine synthesis shows that QPRTase activity is strictly correlated with nicotine content (Wagner and Wagner, *Planta* 165:532 (1985)). Saunders and Bush (*Plant Physiol* 64:236 (1979) showed that the level of QPRTase in the roots of low nicotine mutants is proportional to the levels of nicotine in the leaves.

The present invention encompasses a novel cDNA sequence (SEQ ID NO:1) encoding a plant quinolate phosphoribosyl transferase (QPRTase) of SEQ ID NO:2. As QPRTase activity is strictly correlated with nicotine content, construction of transgenic tobacco plants in which QPRTase levels are lowered in the plant roots (compared to levels in wild-type plants) result in plants having reduced levels of nicotine in the leaves. The present invention provides methods and nucleic acid constructs for producing such transgenic plants, as well as such transgenic plants. Such methods include the expression of antisense NtQPT1 RNA, which lowers the amount of QPRTase in tobacco roots. Nicotine has additionally been found in non-tobacco species and families of plants, though the amount present is usually much lower than in N. tabacum.

The present invention also provides sense and antisense recombinant DNA molecules encoding QPRTase or QPRTase antisense RNA molecules, and vectors comprising those recombinant DNA molecules, as well as transgenic plant cells and plants transformed with those DNA molecules and vectors. Transgenic tobacco cells and plants of this invention are characterized by lower or higher nicotine content than untransformed control tobacco cells and plants.

Tobacco plants with extremely low levels of nicotine production, or no nicotine production, are attractive as recipients for transgenes expressing commercially valuable products such as pharmaceuticals, cosmetic components, or food additives. Tobacco is attractive as a recipient plant for a transgene encoding a desirable product, as tobacco is easily genetically engineered and produces a very large biomass per acre; tobacco plants with reduced resources devoted to nicotine production accordingly will have more resources available for production of transgene products. Methods of transforming tobacco with transgenes producing desired products are known in the art; any suitable technique may be utilized with the low nicotine tobacco plants of the present invention.

Tobacco plants according to the present invention with reduced QPRTase expression and reduced nicotine levels will be desirable in the production of tobacco products having reduced nicotine content. Tobacco plants according to the present invention will be suitable for use in any traditional tobacco product, including but not limited to pipe, cigar and cigarette tobacco, and chewing tobacco, and may be in any form including leaf tobacco, shredded tobacco, or cut tobacco.

The constructs of the present invention may also be useful in providing transgenic plants having increased QPRTase expression and increased nicotine content in the plant. Such constructs, methods using these constructs and the plants so produced may be desirable in the production of tobacco products having altered nicotine content, or in the production of plants having nicotine content increased for its insecticidal effects.

The present inventors have discovered that the TobRD2 gene (see Conkling et al., *Plant Phys.* 93, 1203 (1990)) encodes a Nicotiana 20 tabacum QPRTase, and provide herein the cDNA sequence of NtQPT1 (formerly termed TobRD2) and the amino acid sequence of the encoded enzyme. Comparisons of the NtQPT1 amino acid sequence with the GenBank database reveal limited sequence similarity to bacterial proteins that encode quinolate phosphoribosyl transferase (QPRTase) (FIG. 3).

Quinolate phosphoribosyl transferase is required for de novo nicotine adenine dinucleotide (NAD) biosynthesis in both prokaryotes and eukaryotes. In tobacco, high levels of QPRTase are detected in roots, but not in leaves. To determine that NtQPT1 encoded QPRTase, the present inventors utilized *Escherichia coli* bacterial strain (TH265), a mutant lacking in quinolate phosphoribosyl transferase ($nadC^-$). This mutant cannot grow on minimal medium lacking nicotinic acid. However, expression of the NtQPT1 protein in this bacterial strain conferred the $NadC^+$ phenotype (FIG. 4), confirming that NtQPT1 encodes QPRTase.

Figure 5:
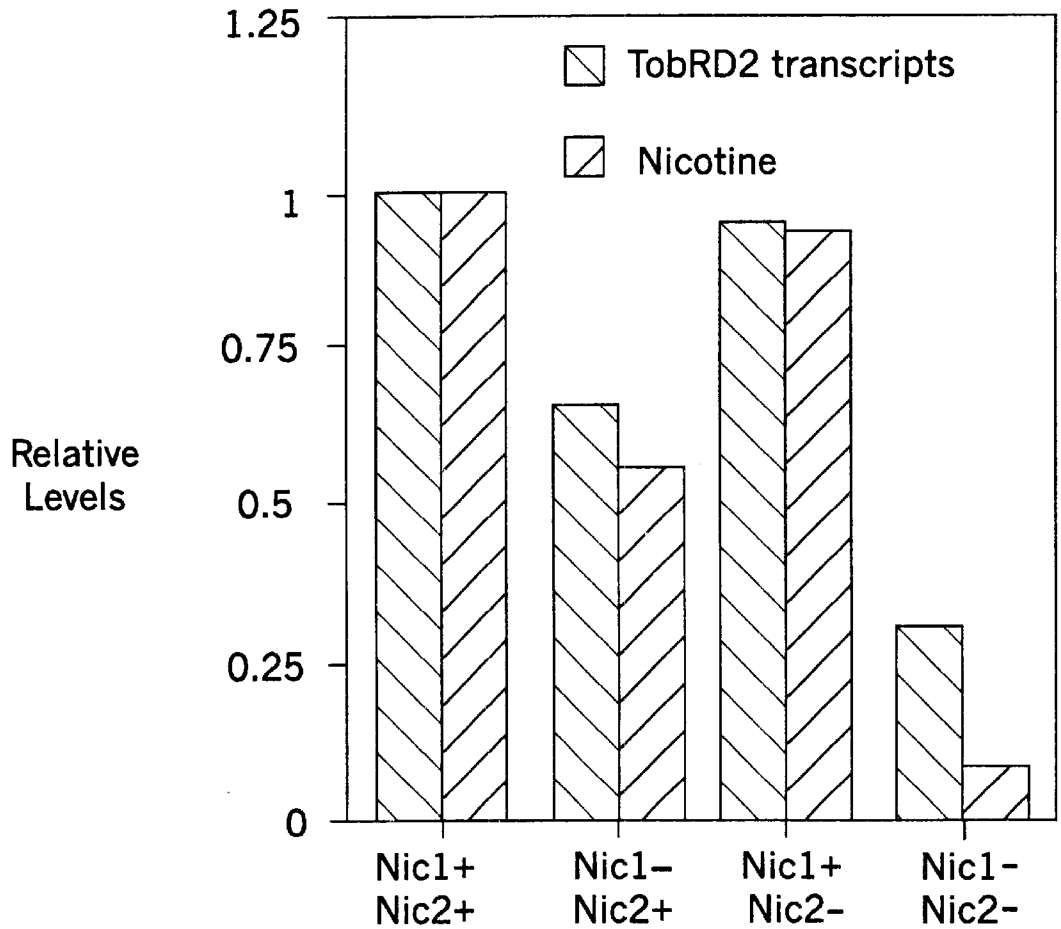
FIG. 5 compares nicotine levels and the relative steady-state NtQTP1 mRNA levels in Nic1 and Nic2 tobacco mutants: wild-type Burley 21 (Nic1/Nic1 Nic2/Nic2); $Nic1^-$ Burley 21 (nic1/nic] Nic2/Nic2); $Nic2^-$ Burley 21 (Nic1/Nic1 nic2/nic2); and $Nic1^-$ $Nic2^-$ Burley 21 (nic1/nic1 nic2/nic2). Solid bars indicate mRNA transcript levels; hatched bars indicate nicotine levels.

The present inventors examined the effects of Nic1 and Nic2 mutants in tobacco, and the effects of topping tobacco plants, on NtQPT1 steady-state mRNA levels and nicotine levels. (Removal of apical dominance by topping at onset of flowering is well known to result in increased levels of nicotine biosynthesis and transport in tobacco, and is a standard practice in tobacco production.) If NtQPT1 is in fact involved in nicotine biosynthesis, it would be expected that (1) NtQPT1 mRNA levels would be lower in Nic1/Nic2 double mutants and (2) NtQPT1 mRNA levels would increase after topping. NtQPT1 mRNA levels in Nic1/Nic2 double mutants were found to be approximately 25% that of wild-type (FIG. 5). Further, within six hours of topping, the NtQPT1 mRNA levels in tobacco plants increased about eight-fold. Therefore, NtQPT1 was determined to be a key regulatory gene in the nicotine biosynthetic pathway.

Transgenic Plant Cells and Plants

Regulation of gene expression in plant cell genomes can be achieved by integration of heterologous DNA under the transcriptional control of a promoter which is functional in the host, and in which the transcribed strand of heterologous DNA is complementary to the strand of DNA that is transcribed from the endogenous gene to be regulated. The introduced DNA, referred to as antisense DNA, provides an RNA sequence which is complementary to naturally produced (endogenous) mRNAs and which inhibits expression of the endogenous mRNA. The mechanism of such gene expression regulation by antisense is not completely understood. While not wishing to be held to any single theory, it is noted that one theory of antisense regulation proposes that transcription of antisense DNA produces RNA molecules which bind to and prevent or inhibit transcription of endogenous mRNA molecules.

In the methods of the present invention, the antisense product may be complementary to coding or non-coding (or both) portions of naturally occurring target RNA. The antisense construction may be introduced into the plant cells in any suitable manner, and may be integrated into the plant genome for inducible or constitutive transcription of the antisense sequence. See, e.g., U.S. Pat. Nos. 5,453,566 and 5,107,065 to Shewmaker et al. (incorporated by reference herein in their entirety). As used herein, exogenous or heterologous DNA (or RNA) refers to DNA (or RNA) which has been introduced into a cell (or the cell's ancestor) through the efforts of humans. Such heterologous DNA may be a copy of a sequence which is naturally found in the cell being transformed, or fragments thereof.

To produce a tobacco plant having decreased QPRTase levels, and thus lower nicotine content, than an untransformed control tobacco plant, a tobacco cell may be transformed with an exogenous QPRT antisense transcriptional unit comprising a partial QPRT cDNA sequence, a full-length QPRT cDNA sequence, a partial QPRT chromosomal sequence, or a full-length QPRT chromosomal sequence, in the antisense orientation with appropriate operably linked regulatory sequences. Appropriate regulatory sequences include a transcription initiation sequence ("promoter") operable in the plant being transformed, and a polyadenylation/transcription termination sequence. Standard techniques, such as restriction mapping, Southern blot hybridization, and nucleotide sequence analysis, are then employed to identify clones bearing QPRTase sequences in the antisense orientation, operably linked to the regulatory sequences. Tobacco plants are then regenerated from successfully transformed cells. It is most preferred that the antisense sequence utilized be complementary to the endogenous sequence, however, minor variations in the exogenous and endogenous sequences may be tolerated. It is preferred that the antisense DNA sequence be of sufficient sequence similarity that it is capable of binding to the endogenous sequence in the cell to be regulated, under stringent conditions as described below.

Antisense technology has been employed in several laboratories to create transgenic plants characterized by lower than normal amounts of specific enzymes. For example, plants with lowered levels of chalcone synthase, an enzyme of a flower pigment biosynthetic pathway, have been produced by inserting a chalcone synthase antisense gene into the genome of tobacco and petunia. These transgenic tobacco and petunia plants produce flowers with lighter than normal coloration (Van der Krol et al., "An Anti-Sense Chalcone Synthase Gene in Transgenic Plants Inhibits Flower Pigmentation", *Nature*, 333, pp. 866–69 (1988)). Antisense RNA technology has also been successfully employed to inhibit production of the enzyme polygalacturonase in tomatoes (Smith et al., "Antisense RNA Inhibition of Polygalacturonase Gene Expression in Transgenic Tomatoes", *Nature*, 334, pp. 724–26 (1988); Sheehy et al., "Reduction of Polygalacturonase Activity in Tomato Fruit by Antisense RNA", *Proc. Nati. Acad Sci. USA*, 85, pp. 8805–09 (1988)), and the small subunit of the enzyme ribulose bisphosphate carboxylase in tobacco (Rodermel et al., "Nuclear-Organelle Interactions: Nuclear Antisense Gene Inhibits Ribulose Bisphosphate Carboxylase Enzyme Levels in Transformed Tobacco Plants", *Cell*, 55, pp. 673–81 (1988)). Alternatively, transgenic plants characterized by greater than normal amounts of a given enzyme may be created by transforming the plants with the gene for that enzyme in the sense (i.e., normal) orientation. Levels of nicotine in the transgenic tobacco plants of the present invention can be detected by standard nicotine assays. Transformed plants in which the level of QPRTase is reduced compared to untransformed control plants will accordingly have a reduced nicotine level compared to the control; transformed plants in which the level of QPRTase is increased compared to untransformed control plants will accordingly have an increased nicotine level compared to the control.

The heterologous sequence utilized in the antisense methods of the present invention may be selected so as to produce an RNA product complementary to the entire QPRTase mRNA sequence, or to a portion thereof. The sequence may be complementary to any contiguous sequence of the natural messenger RNA, that is, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the 3'-terminus of the coding region, or complementary to the 3'-untranslated region of the mRNA. Suitable antisense sequences may be from at least about 13 to about 15 nucleotides, at least about 16 to about 21 nucleotides, at least about 20 nucleotides, at least about 30 nucleotides, at least about 50 nucleotides, at least about 75 nucleotides, at least about 100 nucleotides, at least about 125 nucleotides, at least about 150 nucleotides, at least about 200 nucleotides, or more. In addition, the sequences may be extended or shortened on the 3' or 5' ends thereof.

The particular anti-sense sequence and the length of the anti-sense sequence will vary depending upon the degree of inhibition desired, the stability of the anti-sense sequence, and the like. One of skill in the art will be guided in the selection of appropriate QPRTase antisense sequences using techniques available in the art and the information provided herein. With reference to FIG. 2A and SEQ ID NO: 1 herein, an oligonucleotide of the invention may be a continuous fragment of the QPRTase cDNA sequence in antisense orientation, of any length that is sufficient to achieve the desired effects when transformed into a recipient plant cell.

The present invention may also be used in methods of sense co-suppression of nicotine production. Sense DNAs employed in carrying out the present invention are of a length sufficient to, when expressed in a plant cell, suppress the native expression of the plant QPRTase protein as described herein in that plant cell. Such sense DNAs may be essentially an entire genomic or complementary DNA encoding the QPRTase enzyme, or a fragment thereof with such fragments typically being at least 15 nucleotides in length. Methods of ascertaining the length of sense DNA that results in suppression of the expression of a native gene in a cell are available to those skilled in the art.

In an alternate embodiment of the present invention, Nicotiana 30 plant cells are transformed with a DNA construct containing a DNA segment encoding an enzymatic RNA molecule (i.e., a "ribozyme"), which enzymatic RNA molecule is directed against (i.e., cleaves) the mRNA transcript of DNA encoding plant QPRTase as described herein. Ribozymes contain substrate binding domains that bind to accessible regions of the target mRNA, and domains that catalyze the cleavage of RNA, preventing translation and protein production. The binding domains may comprise antisense sequences complementary to the target mRNA sequence; the catalytic motif may be a hammerhead motif or other motifs, such as the hairpin motif. Ribozyme cleavage sites within an RINA target may initially be identified by scanning the target molecule for ribozyme cleavage sites (e.g., GUA, GUU or GUC sequences). Once identified, short RNA sequences of 15, 20, 30 or more ribonucleotides corresponding to the region of the target gene containing the cleavage site may be evaluated for predicted structural features. The suitability of candidate targets may also be evaluated by testing their accessibility to hybridization with complimentary oligonucleotides, using ribonuclease protection assays as are known in the art. DNA encoding enzymatic RNA molecules may be produced in accordance with known techniques. See, e.g., T. Cech et al., U.S. Pat. No. 4,987,071; Keene et al., U.S. Pat. No. 5,559,021; Donson et al., U.S. Pat. No. 5,589,367; Torrence et al., U.S. Pat. No. 5,583,032; Joyce, U.S. Pat. No. 5,580,967; Gold et al. U.S. Pat. No. 5,595,877; Wagner et al., U.S. Pat. No. 5,591,601; and U.S. Pat. No. 5,622,854 (the disclosures of which are to be incorporated herein by reference in their entirety). Production of such an enzymatic RNA molecule in a plant cell and disruption of QPRTase protein production reduces QPRTase activity in plant cells in essentially the same manner as production of an antisense RNA molecule: that is, by disrupting translation of mRNA in the cell which produces the enzyme. The term 'ribozyme' is used herein to describe an RNA-containing nucleic acid that functions as an enzyme (such as an endoribonuclease), and may be used interchangeably with 'enzymatic RNA molecule'. The present invention further includes DNA encoding the ribozymes, DNA encoding ribozymes which has been inserted into an expression vector, host cells containing such vectors, and methods of decreasing QPRTase production in plants using ribozymes.

Nucleic acid sequences employed in carrying out the present invention include those with sequence similarity to SEQ ID NO:1, and encoding a protein having quinolate phosphoribosyl transferase activity. This definition is intended to encompass natural allelic variations in QPRTase proteins. Thus, DNA sequences that hybridize to DNA of SEQ ID NO:1 and code for expression of QPRTase, particularly plant QPRTase enzymes, may also be employed in carrying out the present invention.

Multiple forms of tobacco QPRT enzyme may exist. Multiple forms of an enzyme may be due to post-translational modification of a single gene product, or to multiple forms of the NtQPT1 gene.

Conditions which permit other DNA sequences which code for expression of a protein having QPRTase activity to hybridize to DNA of SEQ ID NO:1 or to other DNA sequences encoding the protein given as SEQ ID NO:2 can be determined in a routine manner. For example, hybridization of such sequences may be carried out under conditions of reduced stringency or even stringent conditions (e.g., conditions represented by a wash stringency of 0.3 M NaCl, 0.03 M sodium citrate, 0.1% SDS at 60° C. or even 70° C. to DNA encoding the protein given as SEQ ID NO:2 herein in a standard in situ hybridization assay. See J. Sambrook et al., Molecular Cloning, A Laboratory Manual (2d Ed. 1989) (Cold Spring Harbor Laboratory)). In general, such sequences will be at least 65% similar, 75% similar, 80% similar, 85% similar, 90% similar, or even 95% similar, or more, with the sequence given herein as SEQ ID NO:1, or DNA sequences encoding proteins of SEQ ID NO:2. (Determinations of sequence similarity are made with the two sequences aligned for maximum matching; gaps in either of the two sequences being matched are allowed in maximizing matching. Gap lengths of 10 or less are preferred, gap lengths of 5 or less are more preferred, and gap lengths of 2 or less still more preferred.)

Differential hybridization procedures are available which allow 30 for the isolation of cDNA clones whose mRNA levels are as low as about 0.05% of poly($A^+$)RNA. See M. Conkling et al., *Plant Physiol.* 93, 1203–1211 (1990). In brief, cDNA libraries are screened using single-stranded cDNA probes of reverse transcribed mRNA from plant tissue (e.g., roots and/or leaves). For differential screening, a nitrocellulose or nylon membrane is soaked in 5×SSC, placed in a 96 well suction manifold, 150 $\mu$L of stationary overnight culture transferred from a master plate to each well, and vacuum applied until all liquid has passed through the filter. 150 $\mu$L of denaturing solution (0.5M NaOH, 1.5 M NaCl) is placed in each well using a multiple pipetter and allowed to sit about 3 minutes. Suction is applied as above and the filter removed and neutralized in 0.5 M Tris-HCl (pH 8.0), 1.5 M NaCl. It is then baked 2 hours in vacuo and incubated with the relevant probes. By using nylon membrane filters and keeping master plates stored at −70° C. in 7% DMSO, filters may be screened multiple times with multiple probes and appropriate clones recovered after several years of storage.

As used herein, the term 'gene' refers to a DNA sequence that incorporates (1) upstream (5') regulatory signals including the promoter, (2) a coding region specifying the product, protein or RNA of the gene, (3) downstream (3') regions including transcription termination and polyadenylation signals and (4) associated sequences required for efficient and specific expression.

The DNA sequence of the present invention may consist essentially of the sequence provided herein (SEQ ID NO:1), or equivalent nucleotide sequences representing alleles or polymorphic variants of these genes, or coding regions thereof.

Use of the phrase "substantial sequence similarity" in the present specification and claims means that DNA, RNA or amino acid sequences which have slight and non-consequential sequence variations from the actual sequences disclosed and claimed herein are considered to be equivalent to the sequences of the present invention. In this regard, "slight and non-consequential sequence variations" mean that "similar" sequences (i.e., the sequences that have substantial sequence similarity with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

DNA sequences provided herein can be transformed into a variety of host cells. A variety of suitable host cells, having desirable growth and handling properties, are readily available in the art.

Use of the phrase "isolated" or "substantially pure" in the present specification and claims as a modifier of DNA, RNA, polypeptides or proteins means that the DNA, RNA, polypeptides or proteins so designated have been separated from their in vivo cellular environments through the efforts of human beings. As used herein, a "native DNA sequence" or "natural DNA sequence" means a DNA sequence which can be isolated from non-transgenic cells or tissue. Native DNA sequences are those which have not been artificially altered, such as by site-directed mutagenesis. Once native DNA sequences are identified, DNA molecules having native DNA sequences may be chemically synthesized or produced using recombinant DNA procedures as are known in the art. As used herein, a native plant DNA sequence is that which can be isolated from non-transgenic plant cells or tissue. As used herein, a native tobacco DNA sequence is that which can be isolated from non-transgenic tobacco cells or tissue DNA constructs, or "transcription cassettes," of the present invention include, 5, to 3' in the direction of transcription, a promoter as discussed herein, a DNA sequence as discussed herein operatively associated with the promoter, and, optionally, a termination sequence including stop signal for RNA polymerase and a polyadenylation signal for polyadenylase. All of these regulatory regions should be capable of operating in the cells of the tissue to be transformed. Any suitable termination signal may be employed in carrying out the present invention, examples thereof including, but not limited to, the nopaline synthase (nos) terminator, the octapine synthase (ocs) terminator, the CaMV terminator, or native termination signals derived from the same gene as the transcriptional initiation region or derived from a different gene. See, e.g., Rezian et al. (1988) supra, and Rodermel et al. (1988), supra.

The term "operatively associated," as used herein, refers to DNA sequences on a single DNA molecule which are associated so that the function of one is affected by the other. Thus, a promoter is operatively associated with a DNA when it is capable of affecting the transcription of that DNA (i.e., the DNA is under the transcriptional control of the promoter). The promoter is said to be "upstream" from the DNA, which is in turn said to be "downstream" from the promoter.

The transcription cassette may be provided in a DNA construct which also has at least one replication system. For convenience, it is common to have a replication system fictional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; may provide complementation, by imparting prototrophy to an auxotrophic host; or may provide a visible phenotype through the production of a novel compound in the plant.

The various fragments comprising the various constructs, transcription cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature as exemplified by J. Sambrook et al., Molecular Cloning, A Laboratory Manual (2d Ed. 1989)(Cold Spring Harbor Laboratory).

Vectors which may be used to transform plant tissue with nucleic acid constructs of the present invention include both Agrobacterium vectors and ballistic vectors, as well as vectors suitable for DNA-mediated transformation.

The term 'promoter' refers to a region of a DNA sequence that incorporates the necessary signals for the efficient expression of a coding sequence. This may include sequences to which an RNA polymerase binds but is not limited to such sequences and may include regions to which other regulatory proteins bind together with regions involved in the control of protein translation and may include coding sequences.

Promoters employed in carrying out the present invention may be constitutively active promoters. Numerous constitutively active promoters which are operable in plants are available. A preferred example is the Cauliflower Mosaic Virus (CaMV) 35S promoter which is expressed constitutively in most plant tissues. In the alternative, the promoter may be a root-specific promoter or root cortex specific promoter, as explained in greater detail below.

Antisense sequences have been expressed in transgenic tobacco plants utilizing the Cauliflower Mosaic Virus (CaMV) 35S promoter. See, e.g., Cornelissen et al., "Both RNA Level and Translation Efficiency are Reduced by Anti-Sense RNA in Transgenic Tobacco", *Nucleic Acids Res*. 17, pp. 833–43 (1989); Rezaian et al., "Anti-Sense RNAs of Cucumber Mosaic Virus in Transgenic Plants Assessed for Control of the Virus", *Plant Molecular Biology* 11, pp. 463–71 (1988); Rodermel et al., "Nuclear-Organelle Interactions: Nuclear Antisense Gene Inhibits Ribulose Bisphosphate Carboxylase Enzyme Levels in Transformed Tobacco Plants", *Cell* 55, pp. 673–81 (1988); Smith et al., "Antisense RNA Inhibition of Polygalacturonase Gene Expression in Transgenic Tomatoes", *Nature* 334, pp. 724–26 (1988); Van der Krol et al., "An Anti-Sense Chalcone Synthase Gene in Transgenic Plants Inhibits Flower Pigmentation", *Nature* 333, pp. 866–69 (1988).

Use of the CaMV 35S promoter for expression of QPRTase in the transformed tobacco cells and plants of this invention is preferred. Use of the CaMV promoter for expression of other recombinant genes in tobacco roots has been well described (Lam et al., "Site-Specific Mutations Alter In Vitro Factor Binding and Change Promoter Expression Pattern in Transgenic Plants", *Proc. Nat. Acad. Sci. U.S.A* 86, pp. 7890–94 (1989); Pulse et al. "Dissection of 5' Upstream Sequences for Selective Expression of the *Nicotiana plumbaginifolia* rbcS-8B Gene", *Mol. Gen. Genet*. 214, pp. 16–23(1988)).

Other promoters which are active only in root tissues (root specific promoters) are also particularly suited to the methods of the present invention. See, e.g., U.S. Pat. No. 5,459,252 to Conkling et al.; Yamamoto et al., *The Plant Cell*, 3:371 (1991). The TobRD2 root-cortex specific promoter may also be utilized. See, e.g., U.S. patent application Ser. No. 08/508,786, now allowed, to Conkling et al.; PCT WO 9705261. All patents cited herein are intended to be incorporated herein by reference in their entirety.

The QPRTase recombinant DNA molecules and vectors used to produce the transformed tobacco, cells and plants of this invention may further comprise a dominant selectable marker gene. Suitable dominant selectable markers for use in tobacco include, inter alia, antibiotic resistance genes encoding neomycin phosphotransferase (NPTII), hygromycin phosphotransferase (HPT), and chloramphenicol acetyltransferase (CAT). Another well-known dominant selectable marker suitable for use in tobacco is a mutant dihydrofolate reductase gene that encodes methotrexate-resistant dihydrofolate reductase. DNA vectors containing suitable antibiotic resistance genes, and the corresponding antibiotics, are commercially available.

Transformed tobacco cells are selected out of the surrounding population of non-transformed cells by placing the mixed population of cells into a culture medium containing an appropriate concentration of the antibiotic (or other compound normally toxic to tobacco cells) against which the chosen dominant selectable marker gene product confers resistance. Thus, only those tobacco cells that have been transformed will survive and multiply.

Methods of making recombinant plants of the present invention, in general, involve first providing a plant cell capable of regeneration (the plant cell typically residing in a tissue capable of regeneration). The plant cell is then transformed with a DNA construct comprising a transcription cassette of the present invention (as described herein) and a recombinant plant is regenerated from the transformed plant cell. As explained below, the transforming step is carried out by techniques as are known in the art, including but not limited to bombarding the plant cell with microparticles carrying the transcription cassette, infecting the cell with an *Agrobacterium tumefaciens* containing a Ti plasmid carrying the transcription cassette, or any other technique suitable for the production of a transgenic plant.

Numerous Agrobacterium vector systems useful in carrying out the present invention are known. For example, U.S. Pat. No. 4,459,355 discloses a method for transforming susceptible plants, including dicots, with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium vector (i.e., one in which the Agrobacterium contains one plasmid having the vir region of a Ti plasmid but no T region, and a second plasmid having a T region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et al., U.S. Pat. No. 5,015,580. When using ballistic transformation procedures, the transcription cassette may be incorporated into a plasmid capable of replicating in or integrating into the cell to be transformed. Examples of microparticles suitable for use in such systems include 1 to 5 $\mu$m gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art. Fusion of tobacco protoplasts with DNA-containing liposomes or via electroporation is known in the art. (Shillito et al., "Direct Gene Transfer to Protoplasts of Dicotyledonous and Monocotyledonous Plants by a Number of Methods, Including Electroporation", *Methods in Enzymology* 153, pp. 3 13–36 (1987)).

As used herein, transformation refers to the introduction of exogenous DNA into cells, so as to produce transgenic cells stably transformed with the exogenous DNA.

Transformed cells are induced to regenerate intact tobacco plants through application of tobacco cell and tissue culture techniques that are well known in the art. The method of plant regeneration is chosen so as to be compatible with the method of transformation. The stable presence and the orientation of the QPRTase sequence in transgenic tobacco plants can be verified by Mendelian inheritance of the QPRTase sequence, as revealed by standard methods of DNA analysis applied to progeny resulting from controlled crosses. After regeneration of transgenic tobacco plants from transformed cells, the introduced DNA sequence is readily transferred to other tobacco varieties through conventional plant breeding practices and without undue experimentation.

For example, to analyze the segregation of the transgene, regenerated transformed plants ($R_0$) may be grown to maturity, tested for nicotine levels, and selfed to produce $R_1$ plants. A percentage of $R_1$ plants carrying the transgene are homozygous for the transgene. To identify homozygous $R_1$ plants, transgenic $R_1$ plants are grown to maturity and selfed. Homozygous $RI_1$, plants will produce $R_2$ progeny where each progeny plant carries the transgene; progeny of heterozygous $RI_1$, plants will segregate 3:1.

As nicotine serves as a natural pesticide which helps protect tobacco plants from damage by pests. It may therefor be desirable to additionally transform low or no nicotine plants produced by the present methods with a transgene (such as *Bacillus thuringiensis*) that will confer additional insect protection.

A preferred plant for use in the present methods are species of Nicotiana, or tobacco, including *N tabacum, N rustica* and *N glutinosa*. Any strain or variety of tobacco may be used. Preferred are strains that are already low in nicotine content, such as Nic1/Nic2 double mutants.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the transcription cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npill) can be associated with the transcription cassette to assist in breeding.

In view of the foregoing, it will be apparent that plants which may be employed in practicing the present invention include those of the genus Nicotiana.

Those familiar with the recombinant DNA methods described above will recognize that one can employ a full-length QPRTase cDNA molecule or a full-length QPRTase chromosomal gene, joined in the sense orientation, with appropriate operably linked regulatory sequences, to construct transgenic tobacco cells and plants. (Those of skill in the art will also recognize that appropriate regulatory sequences for expression of genes in the sense orientation include any one of the known eukaryotic translation start sequences, in addition to the promoter and polyadenylation/transcription termination sequences described above). Such transformed tobacco plants are characterized by increased levels of QPRTase, and thus by higher nicotine content than untransformed control tobacco plants.

It should be understood, therefore, that use of QPRTase DNA sequences to decrease or to increase levels of QPRT enzyme, and thereby to decrease or increase the nicotine content in tobacco plants, falls within the scope of the present invention.

As used herein, a crop comprises a plurality of plants of the present invention, and of the same genus, planted together in an agricultural field. By "agricultural field" is meant a common plot of soil or a greenhouse. Thus, the present invention provides a method of producing a crop of plants having altered QPTRase activity and thus having increased or decreased nicotine levels, compared to a similar crop of non-transformed plants of the same species and variety.

The examples which follow are set forth to illustrate the present invention, and are not to be construed as limiting thereof.

EXAMPLE 1

Isolation and Sequencing

TobRD2 cDNA (Conkling et al., *Plant Phys.* 93, 1203 (1990)) was sequenced and is provided herein as SEQ ID NO: 1, and the deduced amino acid sequence as SEQ ID NO:2. The deduced amino acid sequence was predicted to be a cytosolic protein. Although plant QPTase genes have not been reported, comparisons of the NtPT1 amino acid sequence with the GenBank database (FIG. 3) revealed limited sequence similarity to certain bacterial and other proteins; quinolate phosphoribosyl transferase (QPRTase) activity has been demonstrated for the *S. typhimurium, E. coli.* and *N tabacum* genes. The NtQPT1 encoded QPTase has similarity to the deduced peptide fragment encoded by an Arabidopsis EST (expression sequence tag) sequence (Genbank Accession number F20096), which may represent part of an Arabidopsis QPTase gene.

EXAMPLE 2

In-Situ Hybridizations

To determine the spatial distribution of TobRD2 mRNA transcripts in the various tissues of the root, in situ hybridizations were performed in untransformed plants. In-situ hybridizations of antisense strand of TobRD2 to the TobRiD2 mRNA in root tissue was done using techniques as described in Meyerowitz, *Plant Mol. Bid. Rep.* 5,242 (1987) and Smith et al., *Plant Mol. Biol. Rep.* 5,237(1987). Seven day old tobacco (*Nicotania tabacum*) seedling roots were fixed in phosphate-buffered glutaraldehyde, embedded in Paraplast Plus (Monoject Inc., St. Louis, Mo.) and sectioned at 8mm thickness to obtain transverse as well as longitudinal sections. Antisense TobRD2 transcripts, synthesized in vitro in the presence of 355-ATP, were used as probes. The labeled RNA was hydrolyzed by alkaline treatment to yield 100 to 200 base mass average length prior to use.

Hybridizations were done in 50% formamide for 16 hours at 42° C., with approximately $5\times10^6$ counts-per-minute (cpm) labeled RNA per milliliter of hybridization solution. After exposure, the slides were developed and visualized under bright and dark field microscopy. The hybridization signal was localized to the cortical layer of cells in the roots (results not shown). Comparison of both bright and dark field images of the same sections localized TobRD2 transcripts to the parenchymatous cells of the root cortex. No hybridization signal was visible in the epidermis or the stele.

EXAMPLE 3

TobRD2 mRNA Levels in Nic1 and Nic2 Tobacco Mutants and Correlation to Nicotine Levels TobRD2 steady-state mRNA levels were examined in Nic1 and Nic2 mutant tobacco plants. Nic1 and Nic2 are known to regulate quinolate phosphoribosyl transferase activity and putrescence methyl-transferase activity, and are co-dominant regulators of nicotine production. The present results are illustrated in FIGS. 5A and 5B show that TobRD2 expression is regulated by Nic1 and Nic2.

RNA was isolated from the roots of wild-type Burley 21 tobacco plants (Nic1/Nic1 Nic2/Nic2); roots of Nic1-Burley 21 (nic1/nic1 Nic2/Nic2); roots of Nic2-Burley 21 (Nic1/Nic] nic2/nic2); and roots of Nic1Nic2-Burley 21 (nic1/nic1 nic2/nic2).

Four Burley 21 tobacco lines (nic) were grown from seed in soil for a month and transferred to hydroponic chambers in aerated nutrient solution in a greenhouse for one month. These lines were isogenic, except for the two low-nicotine loci, and had genotypes of Nic1/Nic1 Nic2/Nic2, Nic1/Nic1 nic2/nic2, nic1/nic1 Nic2/Nic2, nic1/nic1 nic2/nic2. Roots were harvested from about 20 plants for each genotype and pooled for RNA isolation. Total RNA (1 [$\mu$g) from each genotype was electrophoresed through a 1% agarose gel containing 1.1 M formaldehyde and transferred to a nylon membrane according to Sambrook et al. (1989). The membranes were hybridized with $^{32}$P-labeled TobRD2 cDNA fragments. Relative intensity of TobRD2 transcripts were measured by densitometry. FIG. 5 (solid bars) illustrates the relative transcript levels (compared to Nic1/Nic1/Nic2/Nic2) for each of the four genotypes. The relative nicotine content (compared to Nic1/Nic1/Nic2/Nic2) of the four genotypes is shown by the hatched bars.

FIG. 5 graphically compares the relative steady state TobRD2 5 mRNA level, using the level found in wild-type Burley 21 (Nic1/Nic1 Nic2/Nic2) as the reference amount. TobRD2 mRNA levels in Nic1/Nic2 double mutants were approximately 25% that of wild-type tobacco. FIG. 5B further compares the relative levels of nicotine in the near isogenic lines of tobacco studied in this example (solid bars indicate TobRD2 transcript levels; hatched bars indicate nicotine level). There was a close correlation between nicotine levels and TobRD2 transcript levels.

EXAMPLE 4

The Effect of Topping on TobRD2 mRNA Levels

It is well known in the art that removal of the flower head of a tobacco plant (topping) increases root growth and increases nicotine content of the leaves of that plant. Topping of the plant and is a standard practice in commercial tobacco cultivation, and the optimal time for topping a given tobacco plant under a known set of growing conditions can readily be determined by one of ordinary skill in the art.

Figure 6:
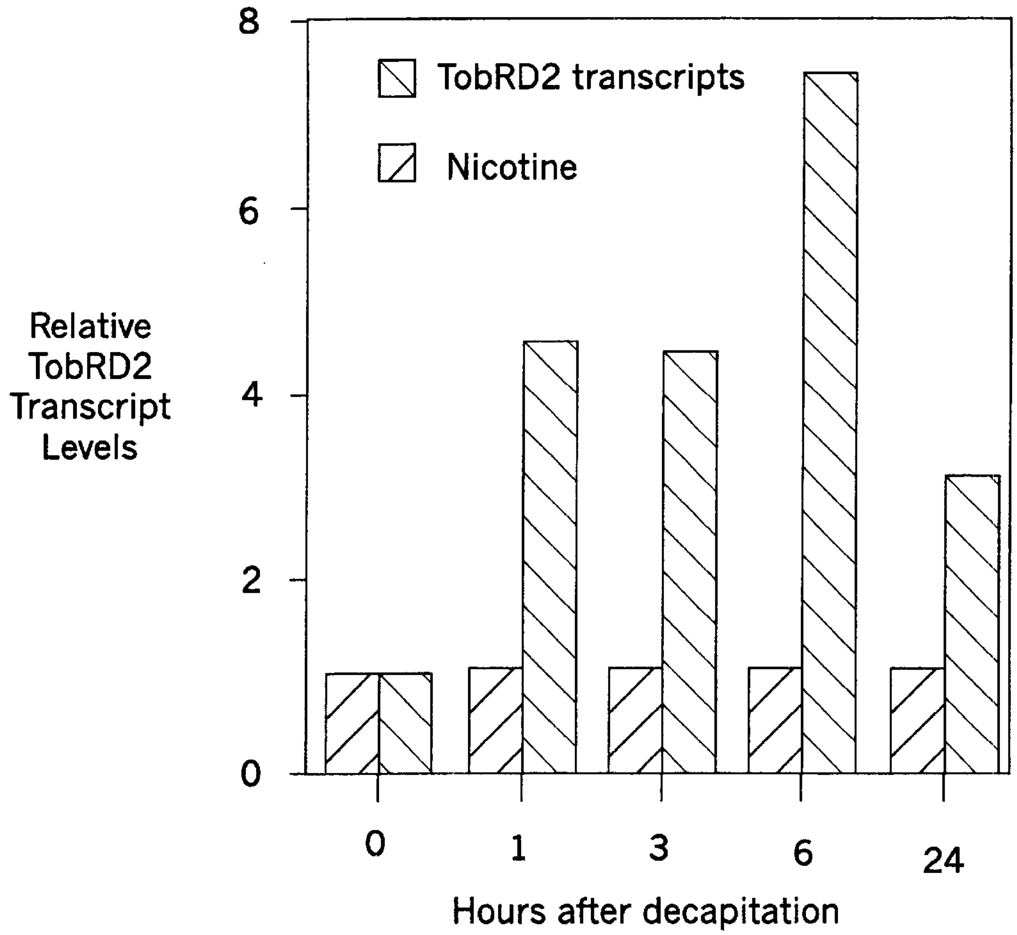
FIG. 6 charts the relative levels of NtQPT1 mRNA over time in topped tobacco plants compared to non-topped control plants. Solid bars indicate mRNA transcript levels; hatched bars indicate nicotine levels.

Tobacco plants (*N tabacum* SRI) were grown from seed in soil for a month and transferred to pots containing sand. Plants were grown in a greenhouse for another two months until they started setting flowers. Flower heads and two nodes were then removed from four plants (topping). A portion of the roots was harvested from each plant after the indicated time and pooled for RNA extraction. Control plants were not decapitated. Total RNA (1 $\mu$g) from each time point was electrophoresed through a 1% agarose gel containing 1.1M formaldehyde and transferred to a nylon membrane according to Sambrook, et al. (1989). The membranes were hybridized with $^{32}$P-labeled TobRD2 cDNA fragments. Relative intensity of TobRD2 transcripts were measured by densitometry. FIG. 6 illustrates the relative transcript levels (compared to zero time) for each time-point with topping (solid bars) or without topping (hatched bars).

Relative TobRD2 levels were determined in root tissue over 24 hours; results are shown in FIG. 6 (solid bars indicate TobRD2 transcript levels in topped plants; hatched bars indicate the TobRD2 transcript levels in non-topped controls). Within six hours of topping of tobacco plants, mRNA levels of TobRD2 increased approximately eight-fold in the topped plants; no increase was seen in control plants over the same time period.

EXAMPLE 5

Complementation of Bacterial Mutant Lackin2 QPRTase with DNA of SEQ ID NO:1

*Escherichia coli* strain TH265 is a mutant lacking quinolate phosphoribosyl transferase (nadC-), and therefor cannot grow on media lacking nicotinic acids.

TH265 cells were transformed with an expression vector (pWS161) containing DNA of SEQ ID NO:1, or transformed with the expression vector (pKK233) only. Growth of the transformed bacteria was compared to growth of TH265 (pKK233) transformants, and to growth of the untransformed TH265 nadC- mutant. Growth was compared on ME minimal media (lacking nicotinic acid) and on ME minimal media with added nicotinic acid.

The *E. coli* strain with the QPTase mutation (nadC), TH265, was kindly provided by Dr. K. T. Hughes (Hughes et al., *J. Bact*. 175:479 (1993). The cells were maintained on LB media and competent cells prepared as described in Sambrook et al (1989). An expression plasmid was constructed in pKK2233 (Brosius, 1984) with the TobRD2 cDNA cloned under the control of the Tac promoter. The resulting plasmid, pWS161, was transformed into TH265 cells. The transformed cells were then plated on minimal media (Vogel and Bonner, 1956) agar plates with or without nicotinic acid (0.0002%) as supplement. TH265 cells alone and TH265 transformed with pKK2233 were plated on similar plates for use as controls.

Figure 4:
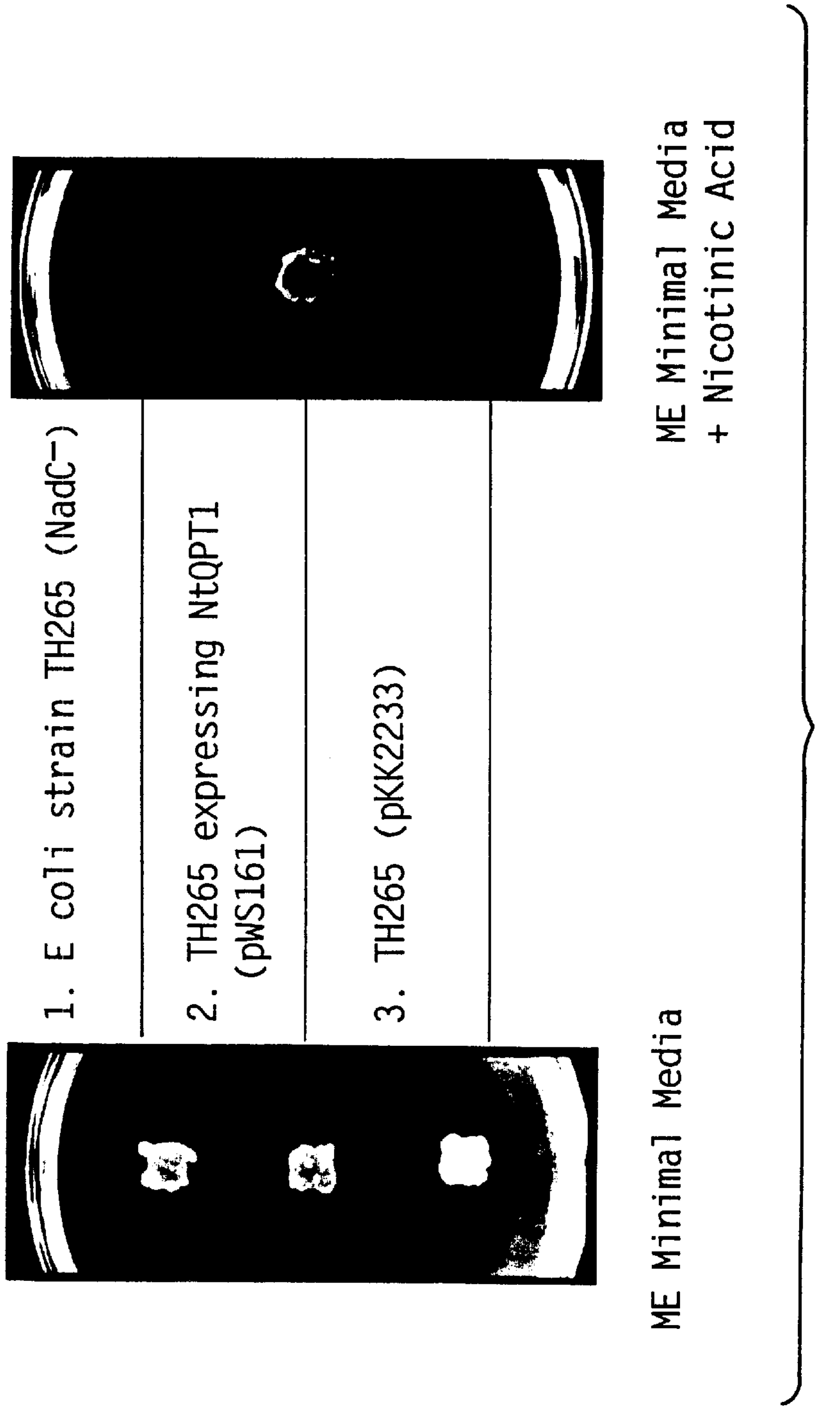
FIG. 4 shows the results of complementation of an *Eseherichia coli* mutant lacking quinolate phosphoribosyl transferase (TH265) with NtQPT1 cDNA. Cells were transformed with an expression vector carrying NtQPT1; growth of transformed TH265 cells expressing NtQPT1 on minimal medium lacking nicotinic acid demonstrated that NtQPT1 encodes QPRTase.

Results are shown in FIG. 4. Only the TH265 transformed with DNA of SEQ ID NO:1 grew in media lacking nicotinic acid. These results show that expression of DNA of SEQ ID NO:1 in TH265 bacterial cells conferred the NadC+ phenotype on these cells, confirming that this sequence encodes QPRTase. The TobRID2 nomenclature was thus changed to NtQPT1.

EXAMPLE 6

Transformation of Tobacco Plants

DNA of SEQ ID NO: 1, in antisense orientation, is operably linked to a plant promoter (CaMV 35S or TobRD2 root-cortex specific promoter) to produce two different DNA cassettes: CaMV35S promoter/antisense SEQ ID NO: 1 and TobRD2 promoter/antisense SEQ ID NO: 1.

A wild-type tobacco line and a low-nicotine tobacco line are selected for transformation, e.g., wild-type Burley 21 tobacco (Nic1+/Nic2+) and homozygous nic1/nic2-Burley 21. A plurality of tobacco plant cells from each line are transformed using each of the DNA cassettes. Transformation is conducted using an Agrobacterium vector, e.g., an *Agrobacterium-binary* vector carrying Ti-border sequences and the nptII gene (conferring resistance to kanamycin and under the control of the nos promoter (nptII)).

Transformed cells are selected and regenerated into transgenic tobacco plants ($R_0$). The $R_0$ plants are grown to maturity and tested for levels of nicotine; a subset of the transformed tobacco plants exhibit significantly lower levels of nicotine compared to non-transforned control plants.

$R_0$plants are then selfed and the segregation of the transgene is analyzed in $R_1$ progeny. $RI_1$progeny are grown to maturity and sefed; segregation of the transgene among $RI_2$progeny indicate which $RI_1$plants are homozygous for the transgene.

What which is claimed:

1. An isolated DNA comprising a DNA sequence selected from the group consisting of:

(a) the DNA sequence of SEQ ID NO: 1;

(b) a DNA sequence which encodes an enzyme having the amino acid sequence of SEQ ID NO: 2; and (c) a DNA sequence which is at least 95% identical to the DNA sequence of (a) or (b) above, and which en codes a quinolate phosphoribosyl transferase enzyme.

2. A DNA construct comprising an expression cassette, which expression cassette comprises, in the 5' to 3' direction, a promoter operable in a plant cell and the DNA according to claim 1 positioned downstream from said promoter and operatively associated therewith.

3. A DNA construct comprising an expression cassette, which expression cassete comprises, in the 5' to 3' direction, a plant promoter and the DNA according to claim 1 positioned downstream from said promoter and operatively associated therewith. said DNA in antisense orientation.

4. A DNA construct comprising, in the 5' to 3' direction, a promoter operable in a plant cell and a DNA encoding a plant quinolate phosphoribosyl transferase having wherein said DNA has the sequence according to SEQ ID NO: 1, said DNA operably associated with said promoter.

5. A DNA construct comprising, in the 5' to 3' direction, a promoter operable in a plant cell and a DNA encoding a plant quinolate phosphoribosyl transferase having sequence according to SEQ ID NO: 1, said DNA in antisense orientation and operably associated with said promoter.

6. The DNA construct according to claim 2, 3, 4 or 5, wherein said promoter is constitutively active in plant cells.

7. The DNA construct according to claim 2, 3, 4 or 5, wherein said promoter is selectively active in plant root tissue cells.

8. The DNA construct according to claim 2, 3, 4 or 5, wherein said promoter is selectively active in plant root cortex tissue cells. vector .

9. The DNA construct according to claim 2, 3, 4 or 5, wherein said construct is a plasmid.

10. A plant transformation vector comprising the DNA construct according to claim 2, 3, 4 or 5.

11. A plant transformation vector comprising DNA construct according to claim 2, 3, 4 or 5, which plant transformation vector is an *Agrobacterium tumefaciens* vector.

12. A plant cell containing the DNA construct according to claim 2, 3, 4 or 5.

13. A transgenic plant comprising the plant cell according to claim 12.

14. A transgenic plant of the species Nicotiana having reduced quinolate phosphoribosyl transferase (QPRTase) expression relative to a non-transformed control plant, said transgenic plant comprising transgenic plant cells containing:

an exogenous DNA construct comprising in the 5' to 3' direction, a promoter operable in said plant cell and a heterologous DNA operably associated with said promoter;

said plant exhibiting reduced QPRTase expression compared to a non-transformed control plant and;

said heterologous DNA comprising a DNA sequence selected from the group consisting of:

(a) the DNA sequence of SEQ ID NO: 1;

(b) a DNA sequence which encodes an enzyme having the anion acid sequence of SEQ ID NO: 2; and (c) a DNA sequence which is at least 95% identical to the DNA sequence of (a) or (b) above, and which en quinolate phosphoribosyl transferase enzyme.

15. The transgenic plant of claim 14, wherein said heterologous DNA is in antisense orientation.

16. The transgenic plant of claim 14, wherein said heterologous DNA is in the sense orientation.

17. A transgenic plant of the species Nicotiana having reduced quinolate phosphoribosyl transferase (QPRTase) expression relative to a non-transformed control plant, wherein said transgenic plant is a progeny of the plant according to claim 14.

18. Seeds of a transgenic plant of the species Nicotiana, said transgenic plant having reduced quinolate phosphoribosyl transferase (QPRTase) expression relative to a non-transformed control plant, wherein said transgenic plant is the plant according to claim 14 or a transgenic progeny plant thereof.

19. A crop comprising the plant species according to claim 14 planted together in an agricultural field.

20. A method of making a transformed plant cell having reduced quinolate phosphoribosyl transferase (QPRTase) expression, said method comprising:

providing a plant cell of a type known to express quinolate phosphoribosyl transferase;

providing an exogenous DNA construct, which construct comprises, in the 5' to 3' direction, a promoter operable in a plant cell and a heterologous DNA operably associated with said promoter; and transforming said plant cell with said DNA construct to produce a transformed plant cell, wherein said transformed plant cell has reduced expression of QPRTase compared to an untransformed cell; and wherein said heterologous DNA comprising a DNA sequence is selected from the group consisting of:

(a) the DNA sequence of SEQ ID) NO: 1;

(b) a DNA sequence which encodes an enzyme having the amino acid sequence of SEQ ID NO: 2; and (c) DNA sequence which is at least 95% (b) above, and which encodes a quinolate phosphoribosyl transferase enzyme.

21. The method of claim 20, wherein said heterologous DNA is in the antisense orientation.

22. The method of claim 20, wherein said heterologous DNA is in the sense orientation.

23. The method of claim 20, wherein said plant cell is *Nicotiana tabacum.*

24. The method of claim 20, further comprising regenerating a plant from said transformed plant cell.

25. The method according to claim 20, wherein said promoter is constitutively active.

26. The method according to claim 20, wherein said promoter is selectively active in plant root tissue cells.

27. The method according to claim 20, wherein said promoter is selectively active in plant root cortex tissue cells.

28. The method according to claim 20, wherein said transforming step comprises bombarding said plant cell with microparticle carrying said DNA construct.

29. The method according to claim 20, wherein said transforming step comprises infecting said plant cell with an *Agrobacterium tumefaciens* containing a Ti plasmid carrying said DNA construct.

30. A method of producing transgenic seeds, comprising collecting seed from the transgenic plant of claim 14.

31. A method for reducing expression of a quinolate phosphoribosyl transferase gene in a plant cell, said method comprising:

growing a plant cell transformed to contain a heterologous DNA, wherein a transcribed strand of said heterologous DNA is complementary to quinolate phosphoribosyl transferase mRNA endogenous to said cell, whereby transcription of said heterologous DNA reduces expression of said quinolate phosphoribosyl gene;

said heterologous DNA comprising a DNA sequence selected from the group consisting of:

(a) the DNA sequence of SEQ ID NO: 1;

(b) a DNA sequence which encodes an enzyme having the amino acid sequence of SEQ ID NO: 2; and (c) a DNA sequence which is at least 95% identical to the DNA sequence of (a) or (b) above, and which en quinolate phosphoribosyl transferase enzyme.

32. A method of producing a tobacco plant having decreased levels of nicotine in leaves of said tobacco plant, said method comprising:

Growing a tobacco plant wherein said plant comprises cells containing a DNA construct comprising a transcriptional initiation region functional in said plant and a heterologous DNA sequence operably joined to said transcriptional initiation region, wherein a transcribed strand of said heterologous DNA sequence is complementary to endogenous quinolate phosphoribosyl transferase messenger RNA cells in said cells;

said heterologous DNA comprising a DNA sequence selected from the group consisting of:

(a) the DNA sequence of SEQ ID NO: 1;

(b) a DNA sequence which encodes an enzyme having the amino acid sequence of SEQ ID NO: 2; and (c) a DNA sequence which is at least 95% identical to the DNA sequence of (a) or (b) above, and which en quinolate phosphoribosyl transferase enzyme.

* * * * *

UNITED STATES PATENT AND TRADEMARK OFFICE

CERTIFICATE OF CORRECTION

PATENT NO. : 6,586,661 B1
DATED : July 1, 2003
INVENTOR(S) : Conkling et al.

It is certified that error appears in the above-identified patent and that said Letters Patent is hereby corrected as shown below:

Column 9,
Line 48, begin a new paragraph after "tissue"

Column 23,
Line 8, delete "en codes" and insert -- encodes --
Line 27, delete "having" and insert -- wherein said DNA has the --
Line 36, delete "vector"
Line 41, insert -- the -- between "comprising" and "DNA"
Line 64, delete "anion" and insert -- amino --
Line 66, delete "en" and insert -- encodes a --

Column 24,
Line 2, insert -- the -- between "in" and "antisense"
Line 33, delete ")"
Line 36, insert -- identical to the DNA sequence of (a) or -- after "95%"
Line 56, delete "microparticle" and insert -- microparticles --

Column 25,
Line 11, delete "en" and insert -- encodes a --

Column 26,
Line 14, delete "en" and insert -- encodes a --

Signed and Sealed this

Tenth Day of February, 2004

Jon W. Dudas

JON W. DUDAS
*Acting Director of the United States Patent and Trademark Office*

UNITED STATES PATENT AND TRADEMARK OFFICE

CERTIFICATE OF CORRECTION

PATENT NO. : 6,586,661 B1
DATED : July 1, 2003
INVENTOR(S) : Conkling et al.

It is certified that error appears in the above-identified patent and that said Letters Patent is hereby corrected as shown below:

Title page,
Item [56], References Cited, the following reference should be added:

-- FOREIGN PATENT DOCUMENTS

EP 0 223 399 B1 --

Signed and Sealed this

Third Day of August, 2004

JON W. DUDAS
*Acting Director of the United States Patent and Trademark Office*